United States Patent
Chanduszko et al.

(10) Patent No.: US 8,992,556 B2
(45) Date of Patent: Mar. 31, 2015

(54) TRANSSEPTAL PUNCTURE APPARATUS

(75) Inventors: Andrzej J. Chanduszko, Weymouth, MA (US); Carol A. Devellian, Topsfield, MA (US)

(73) Assignee: Pressure Products Medical Supplies, Inc., Santa Barbara, CA (US)

( * ) Notice: Subject to any disclaimer, the term of this patent is extended or adjusted under 35 U.S.C. 154(b) by 0 days.

(21) Appl. No.: 13/428,719

(22) Filed: Mar. 23, 2012

(65) Prior Publication Data

US 2012/0179188 A1    Jul. 12, 2012

Related U.S. Application Data

(63) Continuation of application No. 12/652,075, filed on Jan. 5, 2010, now Pat. No. 8,157,829, which is a continuation of application No. 10/841,695, filed on May 7, 2004, now Pat. No. 7,666,203.

(60) Provisional application No. 60/517,983, filed on Nov. 6, 2003.

(51) Int. Cl.
*A61B 17/34* (2006.01)
*A61B 17/00* (2006.01)
*A61B 17/06* (2006.01)

(52) U.S. Cl.
CPC ......... *A61B 17/3468* (2013.01); *A61B 17/0057* (2013.01); *A61B 2017/00243* (2013.01); *A61B 2017/00575* (2013.01); *A61B 2017/06095* (2013.01)
USPC ...................................... 606/185

(58) Field of Classification Search
CPC ........... A61B 17/3468; A61B 17/0057; A61B 2017/00243; A61B 2017/00575; A61B 2017/06095
USPC ............... 606/185, 41, 151, 213, 222, 223; 604/96.1; 600/411
See application file for complete search history.

(56) References Cited

U.S. PATENT DOCUMENTS

| | | | |
|---|---|---|---|
| 3,077,733 A | 2/1963 | Axe |
| 3,103,666 A | 9/1963 | Bone |
| 3,470,834 A | 10/1969 | Bone |
| 3,716,058 A | 2/1973 | Tanner |
| 3,874,388 A | 4/1975 | King |
| 3,875,648 A | 4/1975 | Bone |
| 3,990,619 A | 11/1976 | Russell |

(Continued)

FOREIGN PATENT DOCUMENTS

| | | |
|---|---|---|
| EP | 0553259 A1 | 8/1993 |
| EP | 1013227 A2 | 6/2000 |

(Continued)

OTHER PUBLICATIONS

U.S. Appl. No. 10/841,695, Office Action mailed Aug. 23, 2005.

(Continued)

*Primary Examiner* — Tuan V Nguyen
(74) *Attorney, Agent, or Firm* — RatnerPrestia

(57) ABSTRACT

Devices and methods for performing a transeptal puncture procedure are described. In certain embodiments, the device includes a blunt outer needle, and a second inner needle disposed longitudinally through the lumen of the outer needle, wherein the inner needle is flexible, e.g., has a flexible portion and/or a bend or other non-traumatic conformation at its tip.

26 Claims, 16 Drawing Sheets

(56) References Cited

U.S. PATENT DOCUMENTS

| | | |
|---|---|---|
| 4,006,747 A | 2/1977 | Kronenthal |
| 4,007,743 A | 2/1977 | Blake |
| 4,039,078 A | 8/1977 | Bone |
| 4,235,238 A | 11/1980 | Ogiu |
| 4,394,864 A | 7/1983 | Sandhaus |
| 4,425,908 A | 1/1984 | Simon |
| 4,485,816 A | 12/1984 | Krumme |
| 4,515,583 A | 5/1985 | Sorich |
| 4,556,050 A | 12/1985 | Hodgson |
| 4,586,502 A | 5/1986 | Bedi |
| 4,669,473 A | 6/1987 | Richards |
| 4,696,300 A | 9/1987 | Anderson |
| 4,705,040 A | 11/1987 | Mueller |
| 4,799,483 A | 1/1989 | Kraff |
| 4,800,890 A | 1/1989 | Cramer |
| 4,834,096 A | 5/1989 | Oh |
| 4,836,204 A | 6/1989 | Landymore |
| 4,844,066 A | 7/1989 | Stein |
| 4,915,107 A | 4/1990 | Rebuffat |
| 4,985,014 A | 1/1991 | Orejola |
| 5,021,059 A | 6/1991 | Kensey |
| 5,030,199 A | 7/1991 | Barwick |
| 5,037,433 A | 8/1991 | Wilk |
| 5,041,129 A | 8/1991 | Hayhurst |
| 5,042,976 A | 8/1991 | Ishitsu |
| 5,049,153 A | 9/1991 | Nakao |
| 5,057,114 A | 10/1991 | Wittich |
| 5,073,166 A | 12/1991 | Parks |
| 5,100,432 A * | 3/1992 | Matsutani ............... 606/223 |
| 5,108,420 A | 4/1992 | Marks |
| 5,112,310 A | 5/1992 | Grobe |
| 5,171,259 A | 12/1992 | Inoue |
| 5,190,528 A | 3/1993 | Fonger |
| 5,192,301 A | 3/1993 | Kamiya |
| 5,222,974 A | 6/1993 | Kensey |
| 5,236,440 A | 8/1993 | Hlavacek |
| 5,257,637 A | 11/1993 | El Gazayerli |
| 5,282,827 A | 2/1994 | Kensey |
| 5,284,488 A | 2/1994 | Sideris |
| 5,304,184 A | 4/1994 | Hathaway |
| 5,304,185 A | 4/1994 | Taylor |
| 5,312,341 A | 5/1994 | Turi |
| 5,312,435 A | 5/1994 | Nash |
| 5,320,633 A | 6/1994 | Allen |
| 5,334,217 A | 8/1994 | Das |
| 5,336,252 A | 8/1994 | Cohen |
| 5,354,308 A | 10/1994 | Simon |
| 5,357,979 A | 10/1994 | Imran |
| 5,370,661 A | 12/1994 | Branch |
| 5,403,338 A | 4/1995 | Milo |
| 5,411,481 A | 5/1995 | Allen |
| 5,413,584 A | 5/1995 | Schulze |
| 5,417,699 A | 5/1995 | Klein |
| 5,417,700 A | 5/1995 | Egan |
| 5,425,744 A | 6/1995 | Fagan |
| 5,433,727 A | 7/1995 | Sideris |
| 5,451,235 A | 9/1995 | Lock |
| 5,478,353 A | 12/1995 | Yoon |
| 5,486,185 A | 1/1996 | Freitas |
| 5,486,193 A | 1/1996 | Bourne |
| 5,507,811 A | 4/1996 | Koike |
| 5,540,712 A | 7/1996 | Kleshinski |
| 5,545,138 A | 8/1996 | Fugoso |
| 5,573,542 A | 11/1996 | Stevens |
| 5,577,299 A | 11/1996 | Thompson |
| 5,578,045 A | 11/1996 | Das |
| 5,597,378 A | 1/1997 | Jervis |
| 5,601,571 A | 2/1997 | Moss |
| 5,601,575 A | 2/1997 | Measamer |
| 5,618,311 A | 4/1997 | Gryskiewicz |
| 5,620,461 A | 4/1997 | Muijs Van De Moer |
| 5,634,936 A | 6/1997 | Linden |
| 5,649,959 A | 7/1997 | Hannam |
| 5,683,411 A | 11/1997 | Kavteladze |
| 5,702,421 A | 12/1997 | Schneidt |
| 5,709,707 A | 1/1998 | Lock |
| 5,713,908 A | 2/1998 | Jameel |
| 5,713,952 A | 2/1998 | Vanney |
| 5,720,754 A | 2/1998 | Middleman |
| 5,725,552 A | 3/1998 | Kotula |
| 5,733,294 A | 3/1998 | Forber |
| 5,733,337 A | 3/1998 | Carr |
| 5,741,297 A | 4/1998 | Simon |
| 5,746,765 A | 5/1998 | Kleshinski |
| 5,749,895 A | 5/1998 | Sawyer |
| 5,776,162 A | 7/1998 | Kleshinski |
| 5,797,960 A | 8/1998 | Stevens |
| 5,800,516 A | 9/1998 | Fine |
| 5,810,848 A | 9/1998 | Hayhurst |
| 5,810,884 A | 9/1998 | Kim |
| 5,823,956 A | 10/1998 | Roth |
| 5,827,216 A | 10/1998 | Igo |
| 5,829,447 A | 11/1998 | Stevens |
| 5,836,311 A | 11/1998 | Borst |
| 5,853,422 A | 12/1998 | Huebsch |
| 5,855,614 A | 1/1999 | Stevens |
| 5,861,003 A | 1/1999 | Latson |
| 5,868,753 A | 2/1999 | Schatz |
| 5,879,366 A | 3/1999 | Shaw |
| 5,885,238 A | 3/1999 | Stevens |
| 5,893,856 A | 4/1999 | Jacob |
| 5,895,404 A | 4/1999 | Ruiz |
| 5,902,317 A | 5/1999 | Kleshinski |
| 5,902,319 A | 5/1999 | Daley |
| 5,904,703 A | 5/1999 | Gilson |
| 5,919,200 A | 7/1999 | Stambaugh |
| 5,924,424 A | 7/1999 | Stevens |
| 5,927,284 A | 7/1999 | Borst |
| 5,928,250 A | 7/1999 | Koike |
| 5,935,108 A | 8/1999 | Katoh |
| 5,944,738 A | 8/1999 | Amplatz |
| 5,964,782 A | 10/1999 | Lafontaine |
| 5,976,174 A | 11/1999 | Ruiz |
| 5,989,268 A | 11/1999 | Pugsley |
| 5,993,475 A | 11/1999 | Lin |
| 5,997,556 A | 12/1999 | Tanner |
| 5,997,562 A | 12/1999 | Zadno-Azizi |
| 6,001,085 A | 12/1999 | Lurie |
| 6,007,558 A | 12/1999 | Ravenscroft |
| 6,010,517 A | 1/2000 | Baccaro |
| 6,015,378 A | 1/2000 | Borst |
| 6,024,756 A | 2/2000 | Huebsch |
| 6,030,007 A | 2/2000 | Bassily |
| 6,030,405 A | 2/2000 | Zarbatany |
| 6,042,553 A * | 3/2000 | Solar et al. ............... 600/585 |
| 6,056,760 A | 5/2000 | Koike |
| 6,077,291 A | 6/2000 | Das |
| 6,079,414 A | 6/2000 | Roth |
| 6,080,182 A | 6/2000 | Shaw |
| 6,086,610 A | 7/2000 | Duerig |
| 6,113,609 A | 9/2000 | Adams |
| 6,117,159 A | 9/2000 | Huebsch |
| 6,129,755 A | 10/2000 | Mathis |
| 6,132,438 A | 10/2000 | Fleischman |
| 6,142,975 A | 11/2000 | Jalisi |
| 6,149,664 A | 11/2000 | Kurz |
| 6,152,918 A | 11/2000 | Padilla |
| 6,162,195 A | 12/2000 | Igo |
| 6,162,202 A | 12/2000 | Sicurelli |
| 6,165,183 A | 12/2000 | Kuehn |
| 6,165,204 A | 12/2000 | Levinson |
| 6,171,329 B1 | 1/2001 | Shaw |
| 6,174,322 B1 | 1/2001 | Schneidt |
| 6,200,313 B1 | 3/2001 | Abe |
| 6,206,895 B1 | 3/2001 | Levinson |
| 6,206,907 B1 | 3/2001 | Marino |
| 6,206,912 B1 | 3/2001 | Goldsteen |
| 6,206,921 B1 | 3/2001 | Guagliano |
| 6,214,029 B1 | 4/2001 | Thill |
| 6,217,590 B1 | 4/2001 | Levinson |
| 6,221,092 B1 | 4/2001 | Koike |
| 6,228,097 B1 | 5/2001 | Levinson |
| 6,231,561 B1 | 5/2001 | Frazier |
| 6,245,080 B1 | 6/2001 | Levinson |

(56) References Cited

U.S. PATENT DOCUMENTS

| | | |
|---|---|---|
| 6,254,550 B1 | 7/2001 | McNamara |
| 6,258,026 B1 | 7/2001 | Ravenscroft |
| 6,270,515 B1 | 8/2001 | Linden |
| 6,277,138 B1 | 8/2001 | Levinson |
| 6,277,139 B1 | 8/2001 | Levinson |
| 6,278,371 B1 | 8/2001 | Hopkins |
| 6,287,317 B1 | 9/2001 | Makower |
| 6,290,674 B1 | 9/2001 | Roue |
| 6,302,903 B1 | 10/2001 | Mulier |
| 6,306,150 B1 | 10/2001 | Levinson |
| 6,312,446 B1 | 11/2001 | Huebsch |
| 6,319,263 B1 | 11/2001 | Levinson |
| 6,322,548 B1 | 11/2001 | Payne |
| 6,325,807 B1 | 12/2001 | Que |
| 6,328,688 B1 | 12/2001 | Borst |
| 6,332,877 B1 | 12/2001 | Michels |
| 6,334,843 B1 | 1/2002 | Borst |
| 6,334,872 B1 | 1/2002 | Termin |
| 6,336,898 B1 | 1/2002 | Borst |
| 6,342,064 B1 | 1/2002 | Koike |
| 6,344,049 B1 | 2/2002 | Levinson |
| 6,346,074 B1 | 2/2002 | Roth |
| 6,348,041 B1 | 2/2002 | Klint |
| 6,348,059 B1 | 2/2002 | Hathaway |
| 6,350,229 B1 | 2/2002 | Borst |
| 6,352,531 B1 | 3/2002 | O'Connor |
| 6,352,552 B1 | 3/2002 | Levinson |
| 6,355,052 B1 | 3/2002 | Neuss |
| 6,364,826 B1 | 4/2002 | Borst |
| 6,364,846 B1 | 4/2002 | Nakamura |
| 6,364,853 B1 | 4/2002 | French |
| 6,364,876 B1 | 4/2002 | Erb |
| 6,371,906 B1 | 4/2002 | Borst |
| 6,371,971 B1 | 4/2002 | Tsugita |
| 6,375,625 B1 | 4/2002 | French |
| 6,375,635 B1 | 4/2002 | Moutafis |
| 6,375,671 B1 | 4/2002 | Kobayashi |
| 6,379,342 B1 | 4/2002 | Levinson |
| 6,379,368 B1 | 4/2002 | Corcoran |
| 6,387,104 B1 | 5/2002 | Pugsley |
| 6,394,948 B1 | 5/2002 | Borst |
| 6,398,796 B2 | 6/2002 | Levinson |
| 6,402,772 B1 | 6/2002 | Amplatz |
| 6,440,152 B1 | 8/2002 | Gainor |
| 6,458,100 B2 | 10/2002 | Roue |
| 6,460,749 B1 | 10/2002 | Levinson |
| 6,464,629 B1 | 10/2002 | Boone |
| 6,464,630 B1 | 10/2002 | Borst |
| 6,482,210 B1 | 11/2002 | Skiba |
| 6,482,224 B1 | 11/2002 | Michler |
| 6,488,706 B1 | 12/2002 | Solymar |
| 6,494,888 B1 | 12/2002 | Laufer |
| 6,527,786 B1 | 3/2003 | Davis |
| 6,537,198 B1 | 3/2003 | Vidlund |
| 6,544,274 B2 | 4/2003 | Danitz |
| 6,551,344 B2 | 4/2003 | Thill |
| 6,572,593 B1 | 6/2003 | Daum |
| 6,596,013 B2 | 7/2003 | Yang |
| 6,606,513 B2 | 8/2003 | Lardo |
| 6,623,508 B2 | 9/2003 | Shaw |
| 6,623,518 B2 | 9/2003 | Thompson |
| RE38,335 E | 11/2003 | Aust |
| 6,650,923 B1 | 11/2003 | Lesh |
| 6,652,486 B2 | 11/2003 | Bialecki |
| 6,663,592 B2 | 12/2003 | Rhad |
| 6,685,724 B1 | 2/2004 | Haluck |
| 6,692,471 B2 | 2/2004 | Boudreaux |
| 6,702,835 B2 | 3/2004 | Ginn |
| 6,712,804 B2 | 3/2004 | Roue |
| 6,712,836 B1 | 3/2004 | Berg |
| 6,730,062 B2 | 5/2004 | Hoffman |
| 6,730,081 B1 | 5/2004 | Desai |
| 6,855,124 B1 | 2/2005 | Gonzalez |
| 6,939,348 B2 | 9/2005 | Malecki |
| 7,220,265 B2 | 5/2007 | Chanduszko |
| 7,666,203 B2 | 2/2010 | Chanduszko |
| 7,824,345 B2 | 11/2010 | Euteneuer |
| 8,157,829 B2 * | 4/2012 | Chanduszko et al. ........ 606/185 |
| 8,292,910 B2 * | 10/2012 | Chanduszko et al. ........ 606/185 |
| 2001/0014800 A1 | 8/2001 | Frazier |
| 2001/0034537 A1 | 10/2001 | Shaw |
| 2001/0037129 A1 | 11/2001 | Thill |
| 2001/0039435 A1 | 11/2001 | Roue |
| 2001/0044639 A1 | 11/2001 | Levinson |
| 2001/0049492 A1 | 12/2001 | Frazier |
| 2002/0002373 A1 | 1/2002 | Boehlke |
| 2002/0010481 A1 | 1/2002 | Jayaraman |
| 2002/0019648 A1 | 2/2002 | Akerfeldt |
| 2002/0026094 A1 | 2/2002 | Roth |
| 2002/0026208 A1 | 2/2002 | Roe |
| 2002/0029048 A1 | 3/2002 | Miller |
| 2002/0032462 A1 | 3/2002 | Houser |
| 2002/0043307 A1 | 4/2002 | Ishida |
| 2002/0045908 A1 | 4/2002 | Nobles |
| 2002/0052572 A1 | 5/2002 | Franco |
| 2002/0077555 A1 | 6/2002 | Schwartz |
| 2002/0096183 A1 | 7/2002 | Stevens |
| 2002/0099389 A1 | 7/2002 | Michler |
| 2002/0107531 A1 | 8/2002 | Schreck |
| 2002/0120323 A1 | 8/2002 | Thompson |
| 2002/0128680 A1 | 9/2002 | Pavlovic |
| 2002/0129819 A1 | 9/2002 | Feldman |
| 2002/0169377 A1 | 11/2002 | Khairkhahan |
| 2002/0183786 A1 | 12/2002 | Girton |
| 2002/0183787 A1 | 12/2002 | Wahr |
| 2003/0028213 A1 | 2/2003 | Thill |
| 2003/0045893 A1 | 3/2003 | Ginn |
| 2003/0050665 A1 | 3/2003 | Ginn |
| 2003/0059640 A1 | 3/2003 | Marton |
| 2003/0100920 A1 | 5/2003 | Akin |
| 2003/0139819 A1 | 7/2003 | Beer |
| 2003/0144694 A1 | 7/2003 | Chanduszko |
| 2003/0167055 A1 | 9/2003 | Kolata |
| 2003/0181937 A1 | 9/2003 | Osterlind |
| 2003/0191494 A1 | 10/2003 | Gray |
| 2003/0195530 A1 | 10/2003 | Thill |
| 2003/0195531 A1 | 10/2003 | Gardiner |
| 2003/0208232 A1 | 11/2003 | Blaeser |
| 2003/0212435 A1 | 11/2003 | Gold |
| 2004/0092973 A1 | 5/2004 | Chanduszko |
| 2004/0138701 A1 | 7/2004 | Haluck |
| 2004/0193147 A1 | 9/2004 | Malecki |
| 2004/0230185 A1 | 11/2004 | Malecki |
| 2004/0243122 A1 | 12/2004 | Auth |
| 2004/0267191 A1 | 12/2004 | Gifford, III |
| 2005/0021016 A1 | 1/2005 | Malecki |
| 2005/0034735 A1 | 2/2005 | Deem |
| 2005/0059964 A1 | 3/2005 | Fitz |
| 2005/0065507 A1 | 3/2005 | Hartley |
| 2005/0080406 A1 | 4/2005 | Malecki |
| 2005/0101984 A1 | 5/2005 | Chanduszko |
| 2005/0119675 A1 | 6/2005 | Adams |
| 2005/0131401 A1 | 6/2005 | Malecki |
| 2005/0131460 A1 | 6/2005 | Gifford |
| 2006/0027241 A1 | 2/2006 | Malecki |
| 2006/0074410 A1 | 4/2006 | Malecki |

FOREIGN PATENT DOCUMENTS

| | | |
|---|---|---|
| EP | 1046375 A1 | 10/2000 |
| EP | 0724406 B1 | 12/2001 |
| EP | 1222897 A2 | 7/2002 |
| WO | WO-9206733 A1 | 4/1992 |
| WO | WO-9510983 A1 | 4/1995 |
| WO | WO-9513111 A1 | 5/1995 |
| WO | WO-9807375 A1 | 2/1998 |
| WO | WO-9918862 A1 | 4/1999 |
| WO | WO-9918864 A1 | 4/1999 |
| WO | WO-9918870 A1 | 4/1999 |
| WO | WO-9918871 A1 | 4/1999 |
| WO | WO-9925254 A1 | 5/1999 |
| WO | WO-0027292 A1 | 5/2000 |
| WO | WO-0149185 A1 | 7/2001 |
| WO | WO-0178596 A1 | 10/2001 |

(56) References Cited

FOREIGN PATENT DOCUMENTS

| WO | WO-0241790 A1 | 5/2002 |
|---|---|---|
| WO | WO-03022159 A1 | 3/2003 |
| WO | WO-03059152 A2 | 7/2003 |
| WO | WO-03077733 A2 | 9/2003 |
| WO | WO-03088818 A2 | 10/2003 |
| WO | WO-2004028348 A2 | 4/2004 |

OTHER PUBLICATIONS

U.S. Appl. No. 10/841,695, Office Action mailed Nov. 13, 2008.
International Application Serial No. PCT/US2004/014296, International Search Report and Written Opinion dated Sep. 24, 2004, 6 pgs.
U.S. Appl. No. 10/841,695, Office Action mailed Mar. 18, 2008.
U.S. Appl. No. 10/841,695, Office Action mailed Aug. 22, 2007.
U.S. Appl. No. 10/841,695, Office Action mailed Mar. 28, 2007.
"Elastic Deployment", SMST-2000 Proceedings of the International Conference on Shape Memory and Superelastic Technologies (Apr. 30-May 4, 2000), 3 pgs.
U.S. Appl. No. 10/841,695, Office Action mailed Feb. 13, 2006.
De Ponti, R., "Trans-septal Catheterization for Radiofrequency Catheter Ablation of Cardiac Arrhythmias. Results and Safety of a Simplified Method", European Heart Journal, vol. 19, (Jun. 1998), 943-950.
Hansen, J., "Metals that Remember", Science 81, (1981), pp. 44-47.
Hawkins Jr., I. F., "The Puncture Needle as Guidewire: Needle Guide Technique for Percutaneous Nephrostomy", Seminars in Interventional Radiology 4 (2), (1987), 126-130.
Jackson, C. M., "55-Nitinoi—The Alloy with a Memory: Its Physical Metallurgy, Properties, and Applications: A Report", NASA SP-5110, Washington, D.C.; National Aeronautics and Space Administration (1972), 24-25.

Kimura, A., "Effects of Neutron Irradiation on the Transformation Behavior in Ti-Ni Alloys", Proceedings of the Intl Conf. on Martensitic Transformations (1992), 935-940.
Kotan, Q., "Diameter and Pressure of the Water-Jet for Liver Resection", Easter J. Med. 6(2), (2001), 43-37.
Kramer, P., "PFO and Stroke: The Hidden Connection", Endovascular Today, http://www.evtoday.com/03archive/0903/101.html.
Protsenko, J. A., "Electrosurgical Tissue Resection: a Numerical and Experimental Study", Proceedings of SPIE 4954, (2003), 64-70.
Ramanathan, G., "Experimental and Computational Methods for Shape Memory Alloys", 15th ASCE Engineering Mechanics Conference, (Jun. 2-5, 2002), 12 pgs.
Ruiz, C. E., "The Puncture Technique: A New Method for Transcatheter Closure of Patent Foramen Ovale", Catheter and Cardiovasc. Interv. 53, (2001), 369-372.
Shabalovskaya, S. A., "Surface, Corrosion and Biocompatibility Aspects of Nitinol As an Implant Material", Bio-Medical Materials and Engineering 12 (2002), 69-109.
Sommer, R. J., "New Transseptal Puncture Technique for Transcatheter Closure of Patent Foramen Ovale", Mount Sinai Medical Center, (2002).
Stockel "Nitinol Medical Devices and Implants", SMST-2000: Proceedings of the International Conference on Shape Memory and Superelastic Technologies, 531-540.
Szili-Torok, T., "Transseptal Left Heart Catherisation Guided by Intracardiac Echocardiography", Heart 86:ell, (2001).
Uchil, J., "Shape Memory Alloys—Characterization Techniques", Pramana-Journal of Physics 58(5-6), (2002), 1131-1169.

\* cited by examiner

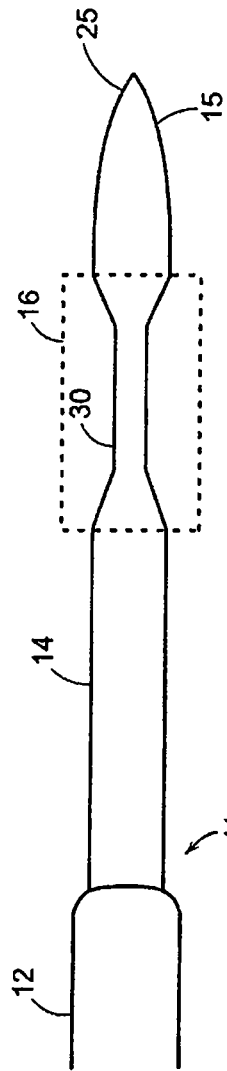
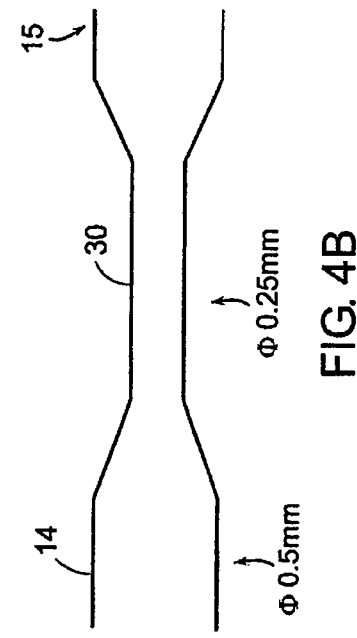
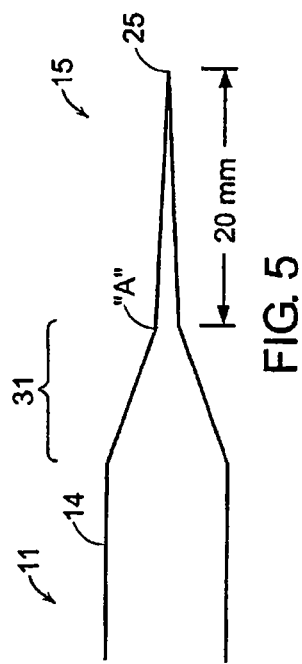
FIG. 4A
FIG. 4B
FIG. 5

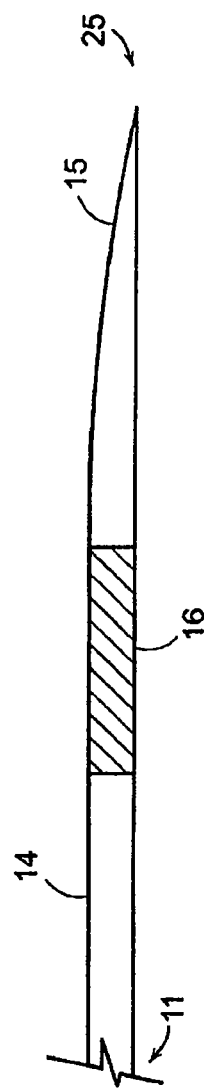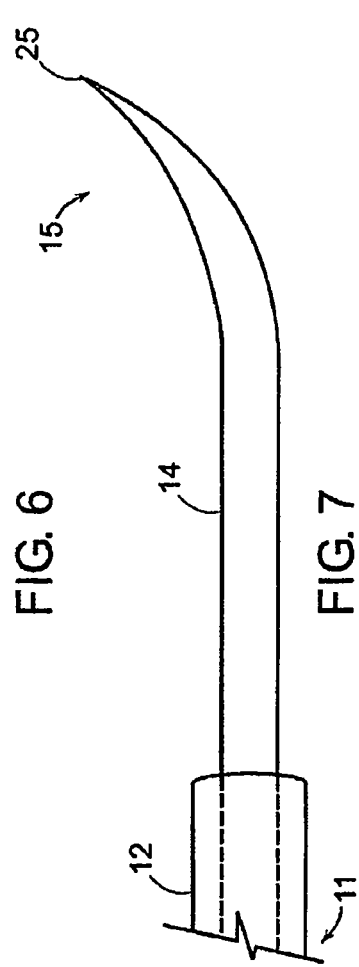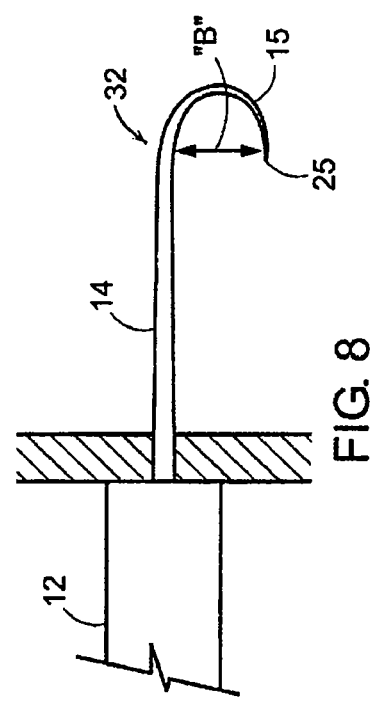
FIG. 6
FIG. 7
FIG. 8

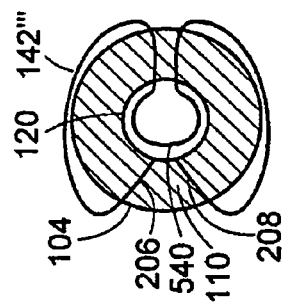
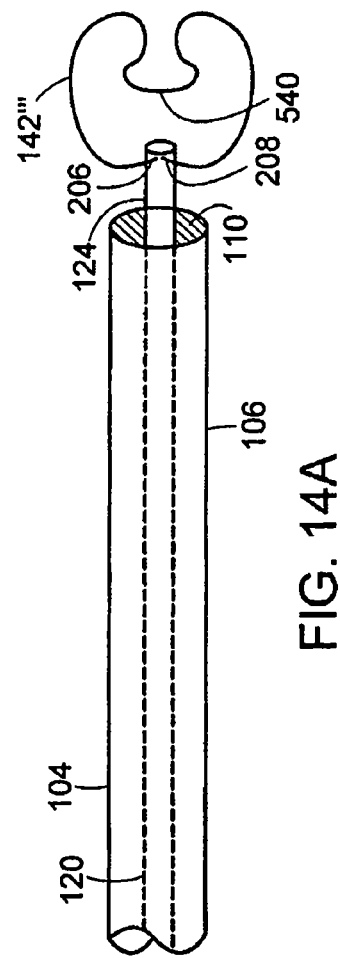
FIG. 14A
FIG. 14B
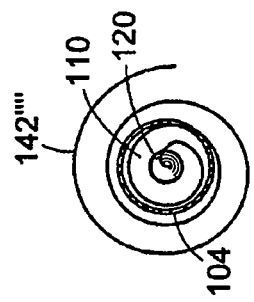
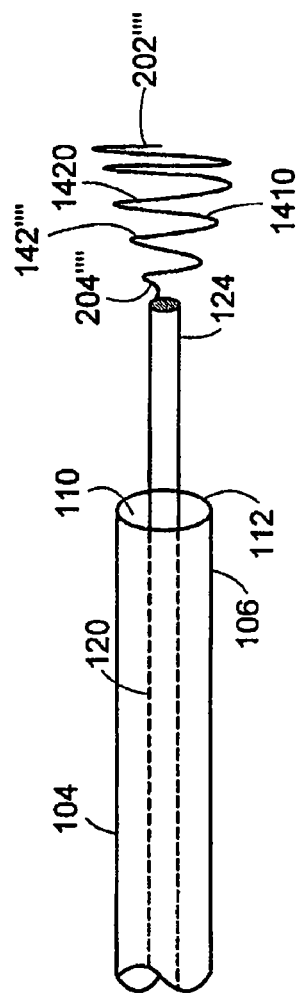
FIG. 15A
FIG. 15B

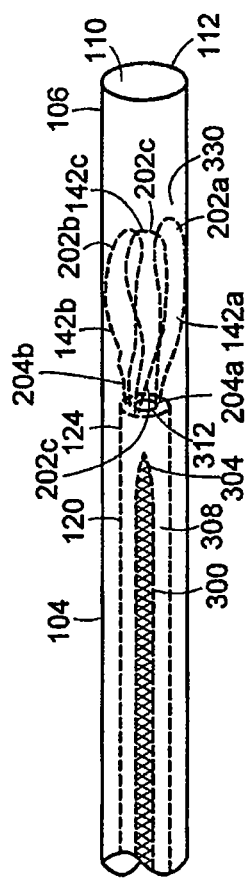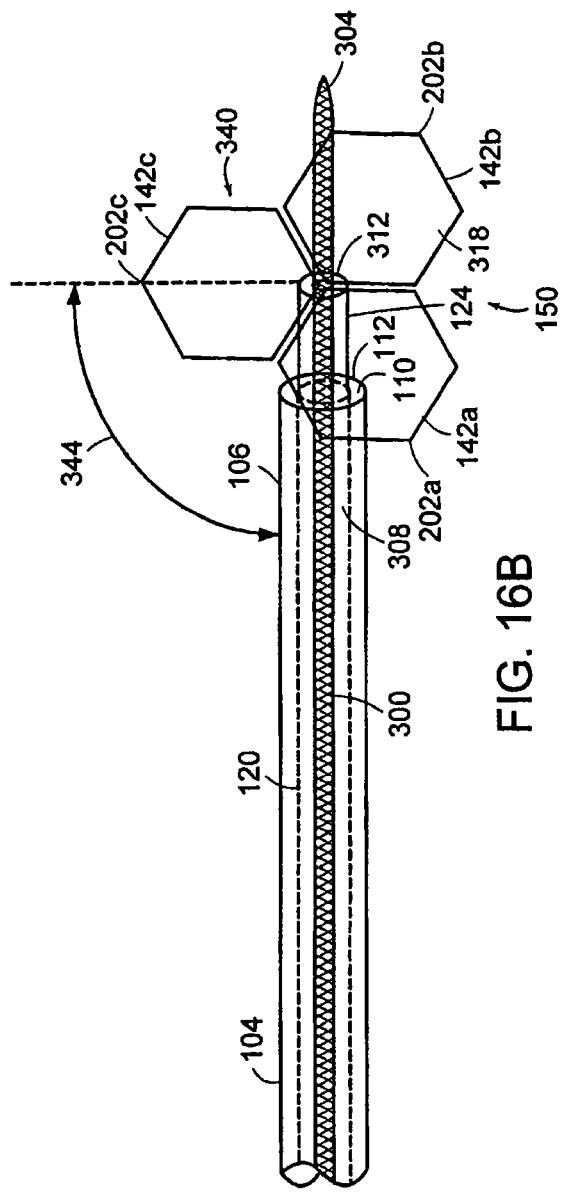
FIG. 16A
FIG. 16B

TRANSSEPTAL PUNCTURE APPARATUS

RELATED APPLICATIONS

"This application is a continuation application of U.S. application Ser. No. 12/652,075, filed Jan. 5, 2010, now U.S. Pat. No. 8,157,829, which is a continuation application of U.S. application Ser. No. 10/841,695, filed May 7, 2004, now U.S. Pat. No. 7,666,203, which claims priority on Provisional Application No. 60/517,983, filed Nov. 6, 2003, which applications are all incorporated by reference herein in their entireties."

FIELD OF THE INVENTION

The invention generally relates to a device for performing an intracardiac transseptal puncture procedure. More specifically, the device relates to transseptal puncture of the atrial septum for the treatment of intracardiac defects such as patent foramen ovale (PFO) and other therapeutic applications for diseases associated with the heart.

BACKGROUND OF THE INVENTION

Septal puncture is utilized in patients in which a communication is present between the two atria of the heart, for example, a patient with a patent foramen ovale (PFO). A PFO consists of two layers of overlapping but unfused tissues, the septum primum and the septum secundum, forming a tunnel like "hole" between the two tissues that can put the patient at a high risk of embolic stroke. Due to the tunnel-like nature of many PFOs, an occlusion device that is used to repair the PFO often does not sit flat on the septal wall when it is implanted, such that a portion of the occluder is positioned in the PFO tunnel. For this reason a second hole in the septum primum part of the atrial septum near the PFO is introduced by septal puncture through which the occlusion device is then positioned (rather than through the PFO tunnel).

Septal puncture through an intact atrial septum from the right atrium to the left atrium is also often necessary. This is traditionally performed using rigid, long needles, such as Brockenbrough or Ross needles. In all types of septal puncture, the needle that is used to puncture the atrial septum poses a high risk of inadvertent puncture through tissue other than the septum primum, for example, the atrial free wall, posing a significant risk to the patient. For PFO closure, this risk is potentially even higher, due to the fact that the septal tissue is defective and often thinning, and may stretch an even greater amount during the puncture procedure, bringing the tip of the needle dangerously close to the atrial free wall or the left atrial appendage.

A device and method that permits the surgeon to safely puncture both an intact atrial septum and an atrial septum having a PFO is therefore needed.

SUMMARY OF THE INVENTION

The invention relates generally to devices and methods for performing a transseptal puncture procedure that are safe alternatives to those currently being performed.

In one aspect, the invention relates to a device for puncturing the atrial septum of a patient. In one embodiment of the invention, the device includes a first, outer needle with a blunt distal end and a lumen longitudinally disposed therethrough and a second, inner needle axially disposed in the lumen of the outer needle. In an embodiment, the inner needle has a proximal portion, an intermediate portion, and a distal portion, wherein the intermediate portion is more flexible than either the proximal portion or the distal portion of the inner needle.

In an embodiment, the intermediate portion is a segment that is approximately 20 mm from the distal end of the inner needle. The intermediate portion may be, for example, 3 mm in length. In an embodiment, the intermediate portion has a waist. The waist of the intermediate portion is, for example, about 0.2 mm in diameter. In a particular embodiment, the intermediate portion of the inner needle may be made of a polymer.

In another embodiment, the inner needle has a distal portion and a proximal portion, wherein the distal portion is more flexible than the proximal portion. In another embodiment, the inner needle is flexible in both the distal portion and the proximal portion (e.g., has homogeneous flexibility).

As another feature, the distal portion of the inner needle has a distal portion that deviates from the linear path of the inner needle such as, for example, a taper, a bend, a curve, a cork screw or a hook. In a particular embodiment, the tip of the inner needle is turned inward during the delivery procedure to avoid the risk of inadvertent puncture of tissue. In another embodiment, the inner needle contains a portion that has a different thickness or diameter than the rest of the inner needle such as, for example, a tapered portion, whereby the inner needle is tapered from one thickness to another.

In an embodiment, the distal portion of the outer needle is more flexible than the proximal portion of the outer needle.

In still another embodiment, the device includes a outer needle with a blunt distal end and a lumen axially disposed therethrough and a pump for introducing a high pressure jet spray through the lumen of the outer needle.

In a further embodiment of the invention, the device has a outer needle with a blunt distal end and an insulating material for insulating the length of the proximal and intermediate portion, leaving the distal tip of the outer needle uninsulated. As an additional feature, the device may include unipolar electrodes or, alternatively, the device may include bipolar electrodes.

In another aspect, the invention provides a method for puncturing the atrial septum of a patient's heart by accessing the right atrium via a vessel. The method includes introducing into the right atrium a transseptal puncture device that includes a first outer needle with a blunt distal end and a lumen longitudinally disposed therethrough and a second inner needle axially disposed in the lumen of the outer needle, the inner needle having a proximal portion, a distal portion, and an intermediate portion that is more flexible than the proximal portion or the distal portion. The outer needle is contacted with the atrial septum and the inner needle is pushed through the septum in advance of the outer needle. A delivery sheath is then positioned using a standard catheterization laboratory technique in the left atrium and the transseptal puncture device is withdrawn from the patient's body.

In another aspect, the invention provides a method for puncturing the atrial septum of a patient's heart by accessing the right atrium via a vessel. The method includes introducing into the right atrium a transseptal puncture device that includes a first, outer needle with a blunt distal end and a lumen longitudinally disposed therethrough and a second, inner needle axially disposed in the lumen of the outer needle, the inner needle having a proximal portion and a distal portion, wherein the distal portion is more flexible than the proximal portion. The outer needle is first contacted with the atrial septum. The inner needle is then pushed through the septum in advance of the outer needle. A delivery sheath is positioned in the left atrium and the transseptal puncture device is withdrawn from the patient's body.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the invention.

FIG. 4A is a longitudinal view of the distal end of an inner needle of a transseptal puncture device according to an illustrative embodiment of the invention in which the intermediate portion contains a waist.

FIG. 4B is an exploded view of the intermediate portion of FIG. 4A.

FIG. 5 is a longitudinal view of the distal end of an inner needle of a transseptal puncture device according to another illustrative embodiment of the invention in which the inner needle has a tapered intermediate portion.

FIG. 6 is a longitudinal view of the distal end of an inner needle of a transseptal puncture device according to another illustrative embodiment of the invention, in which the inner needle has an intermediate portion.

FIG. 7 is a longitudinal view of the distal end of an inner needle of a transseptal puncture device according to another illustrative embodiment of the invention in which the distal tip of the inner needle is bent.

FIG. 8 is a longitudinal view of the distal end of an inner needle of a transseptal puncture device according to another illustrative embodiment of the invention in which the distal end of the inner needle has a hook.

FIG. 14A is a schematic side view of an embodiment of a flexible member according to the invention.

FIG. 14B is a schematic end-on view of the flexible member of FIG. 14A.

FIG. 15A is a schematic side view of an embodiment of a flexible member according to the invention.

FIG. 15B is a schematic end-on view of the flexible member of FIG. 15A.

FIG. 16A is a schematic side view of an embodiment of a set of flexible members, a cutting member, and an elongate member of a portion of a septal puncture apparatus according to the invention.

FIG. 16B is an illustration of the set of flexible members and the cutting member extended out of the elongate member of FIG. 16A.

DETAILED DESCRIPTION OF THE INVENTION

The invention described herein relates to devices and methods for puncturing the atrial septum via the percutaneous route for the treatment of intracardiac defects such as, for example, patent foramen ovale, intracardiac sources of emboli that may cause embolic stroke, and defects related to cardiac disease.

Figure 1:
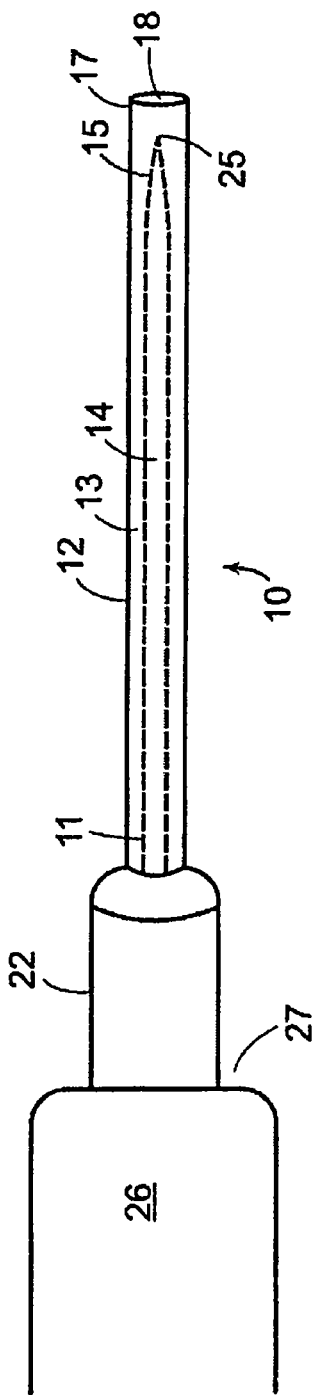
FIG. 1 is a plan view of a transseptal puncture device according to an illustrative embodiment of the invention.

In one aspect, the invention relates to a percutaneous device for making a transseptal puncture in the atrial septum of the heart. FIG. 1 is a plan view of the transseptal puncture device according to an illustrative embodiment of the invention. The illustrative percutaneous device 10 includes a first, outer needle 12 including a lumen 13 axially disposed along the long axis of the outer needle 12 and including a blunt distal end 17 having an opening 18. A second, inner needle 14 is axially disposed within the lumen of the outer needle 12. The outer needle 12 provides structural support for the inner needle 14 and also functions as a dilator of the hole created in the atrial wall by the inner needle 14. The device 10 may further feature a transcutaneous intravascular sheath 22 through which the device 10 passes from outside the patient's body through a vessel, for example, the femoral vein, through the inferior vena cava to the right atrium, and a control handle 26 at the distal end 27 of the sheath 22. The sheath and/or other components of the delivery system may be steerable by actuators (not shown) on the control handle 26 to aid in delivering the device along the tortuous vascular path leading to the patient's right atrium. In certain embodiments, the distal end 17 of the outer needle 12 is tapered toward the inner needle 14, and the distal end 27 of the sheath 22 is tapered toward the outer needle 12.

In an embodiment, the outer needle 12 is similar in size to a Brockenbrough needle, e.g., with tip diameter of about 0.8 mm. The percutaneous device 10 also features a septal perforator, for example, a second, inner needle 14. Alternatively, the septal perforator is a radio frequency electrode (not shown) that is coupled to the outer needle 12, or is a high pressure jet spray (not shown) that is emitted from the opening 18 of the outer needle 12.

Figure 2:
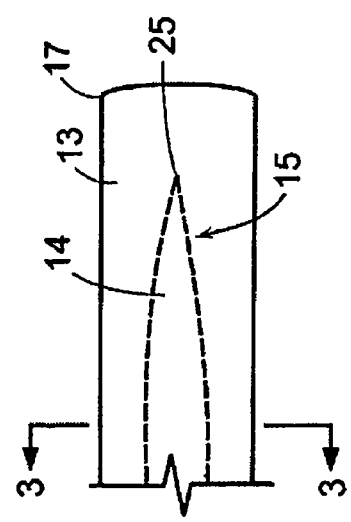
FIG. 2 is a longitudinal plan view of the distal end of a transseptal puncture device according to an illustrative embodiment of the invention.
Figure 3:
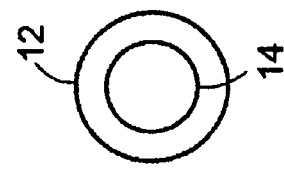
FIG. 3 is a cross sectional view of the distal end of a transseptal puncture device taken along lines 3-3 in FIG. 2.

In an embodiment depicted in FIGS. 2 and 3, the inner needle 14 includes a sharp tip 25 at a distal end 15 of the inner needle 14. The inner needle 14 is axially disposed within the lumen 13 of the outer needle 12. The inner needle 14 is reciprocally and axially moveable in the lumen 13 of the outer needle 12. The inner needle 14 can be rotated as well. The distal end 15 of the inner needle 14 is extendable through the opening 18 at the distal end 17 of the outer needle 12. The inner diameter of the lumen 13 of the outer needle 12 typically approximates the outer diameter of the inner needle 14.

The outer needle 12 and the inner needle 14 are made from various metals such as, for example, nitinol, steel, or titanium, or alloys thereof or polymers such as polyimide, PEBAX®, polyethylene, polytetrafluoroethylene (EPTFE), Fluorinated-ethylenepropylene (FEP), and polyurethane. In one embodiment, the inner needle 14 is solid to increase its sharpness. Alternatively the inner needle 14 is hollow. The use of the outer needle 12 for introducing the inner needle 14 into the patient's cardiac tissue is preferred. In another embodiment, a dilator that is made from material that provides sufficient support during the transseptal puncture procedure is used and the outer needle 12 may not be needed.

FIGS. 4A and 4B are a longitudinal view and an exploded view, respectively, of the distal end of an inner needle of a transseptal puncture device according to another illustrative embodiment of the invention. The illustrative inner needle 14 includes a waist 30 near the distal end 15 of the inner needle 14. The waist 30 is positioned on an intermediate portion 16 of the inner needle 14 that is narrower in diameter than the portion of the inner needle 14 that is proximal to the intermediate portion 16 and the portion of the inner needle 14 that is distal to the intermediate portion 16. The waist 30 is thereby more flexible or bendable than the portions of the inner needle 14 that are proximal or distal to the waist 30. In one embodiment, the distal portion 15 is more flexible than the proximal portion 11 of the inner needle 14. The intermediate portion 16 having waist 30 is positioned about 5 mm to about 30 mm, preferably about 20 mm proximal to the distal end 15 of the inner needle 14. In an embodiment, the diameter of the waist 30 ranges from about 0.1 mm to about 0.5 mm, e.g., if the waist is composed of a metal, while the diameter of the inner needle 14 proximal to the waist 30 ranges from about 0.5 mm to about 1.5 mm and the diameter of the inner needle 14 distal to the waist 30 ranges from about 0.2 mm to about 1 mm. In another embodiment, the diameter of the waist 30 ranges from about 0.1 to about 1 mm, e.g., if the waist is composed of a non-metal, such as, for example, a polymer, such as (PEBAX) or polyurethane, a plastic, rubber, or any other polymer deemed suitable to those skilled in the art. In that case, the diameter of the inner needle 14 proximal to the waist 30 ranges from about 0.5 mm to about 3.0 mm and the diameter of the inner needle 14 distal to the waist 30 ranges from about 0.2 mm to about 3.0 mm. For example, the diameter of the waist 30 is about 0.2 mm, the diameter of the inner needle 14 proximal to the waist 30 is about 1 mm and the diameter of the inner needle 14 distal to the waist 30 is about 0.4 mm.

FIG. 5 is a longitudinal view of the distal end of an inner needle of a transseptal puncture device according to another illustrative embodiment of the invention. In one embodiment, the inner needle 14 diameter is larger (e.g., 1 mm larger) at the proximal end of the inner needle 14 than the distal end 17. Alternatively, the inner needle 14 diameter is larger throughout the length of the inner needle 14 except for the most distal about 20 mm of the distal end 15. In one embodiment, the inner needle 14 contains a portion 31 at the distal end 15 that is tapered or the diameter of the inner needle 14 is gradually stepped down, for example, to a diameter of about 0.1 to about 0.25 mm, preferably about 0.2 mm, at a point "A" about 10 mm to about 20 mm proximal to the tip 25 of the inner needle 14. In an embodiment, the diameter of the inner needle 14 from the tip 25 to the point "A" is uniform. In a particular embodiment, the distal about 10 mm of the inner needle 14 adjacent to the tip 25 has a diameter of about 0.2 mm. According to this embodiment of the invention, the distal end 15 of the inner needle 14 is thinner and therefore is more flexible than the proximal portion 11 of the inner needle 14. In another embodiment the tapered or step-down portion 31 can extend to the tip 25 of the inner needle 14 and can be about 5 mm to about 30 mm long.

FIG. 6 is a longitudinal view of the distal end of an inner needle of a transseptal puncture device according to another illustrative embodiment of the invention. At a position about 5 mm to about 30 mm, preferably about 20 mm from the distal end 15, the inner needle 14 includes an intermediate portion 16 manufactured from, or coated with, a material or treated such that the intermediate portion 16 is more likely to bend than the portions of the inner needle 14 that are proximal 11 and distal 15 to the intermediate portion 16. For example, if the inner needle 14 is composed of nitinol, the intermediate portion 16 may be annealed at 500 degrees Centigrade for 10 minutes to relieve stress in otherwise superelastic nitinol wire in an as drawn condition. Alternatively, the intermediate portion 16 may be made from a softer material than the proximal portion 11 and distal portion 15 of the inner needle 14. For example, the material of the intermediate portion 16 may be a polymer while the proximal portion 11 and distal portion 15 on the inner needle 14 are made from, for example, a rigid metal or, alternatively, a nickel titanium alloy such as nitinol. The intermediate portion 16 may be welded to, crimped or attached by adhesives to the proximal portion 11 and distal portion 15 of the inner needle 14. In one embodiment, the intermediate portion 16 is about 0.5 mm to about 30 mm, preferably about 2 mm in length. Alternatively, geometric modification may make the intermediate portion 16 more flexible, for example, by the introduction of slits, grooves, cut-aways, notches, dimples, or other modification that thins portions of the wall of the intermediate portion 16.

In another embodiment (not shown), the distal, the proximal, and/or the intermediate portion (if present) of the inner needle 14 is flexible.

FIG. 7 is a longitudinal view of the distal end of an inner needle of a transseptal puncture device according to another illustrative embodiment of the invention. The distal end 15 of the illustrative inner needle 14 may be straight (e.g., 0 degrees) or is bent at an angle ranging from about >0 degrees to about 270 degrees, preferably about 180 degrees relative to the long axis of the inner needle 14.

Alternatively, referring to FIG. 8, when the distal end 15 of the inner needle 14 is not constrained within the lumen 13 of the outer needle 12, the distal end 15 has an essentially non-traumatic conformation, such as a helical, curved, cork screw, or hook shape. For example, the diameter "B" of the loop that forms the hook 32 can be between about 5 mm and about 30 mm, preferably about 10 mm. When the distal end 15 is enclosed within the lumen 13 of the outer needle 12, the entire length of the inner needle 14 is substantially straight and parallels the long axis of the outer needle 12.

In an alternative embodiment of the transseptal puncture device, the inner needle is replaced by a pulsating high pressure saline jet (or other suitable fluid) (not shown) generated by a pump. The jet spray is directed to the atrial septum from the distal end of the blunt, outer needle according to the invention and incises the tissue. The outer needle is then gradually advanced through the incision. Because the incision is made gradually and slowly, the method is safer than the currently used methods, for example, because there is a reduced risk of trauma and/or bleeding.

In yet another embodiment of the transseptal puncture device, the blunt, outer needle is replaced by a radio frequency (RF) apparatus (not shown). The outer needle according to the invention is insulated except for the outer needle tip. The alternating current travels down the outer needle. Preferably, unipolar electrodes can be used for the outer needle with grounding pads typically placed on the patient's thighs. Alternatively, a bipolar electrode system can be employed as well. The application of RF to the outer needle increases the tissue temperature around the outer needle tip to over 100 degrees C. Mechanical cohesion in the tissue is diminished and allows the outer needle to be advanced as pressure is applied to the tissue by the outer needle tip. Any other method producing heat (e.g., such as electrical resistance, laser, or ultrasound) can be potentially used instead of RF. As with the saline jet described above, the incision is created slowly therefore the risk of accidental puncture of tissue that is not targeted for incision is minimal.

Figure 9A:
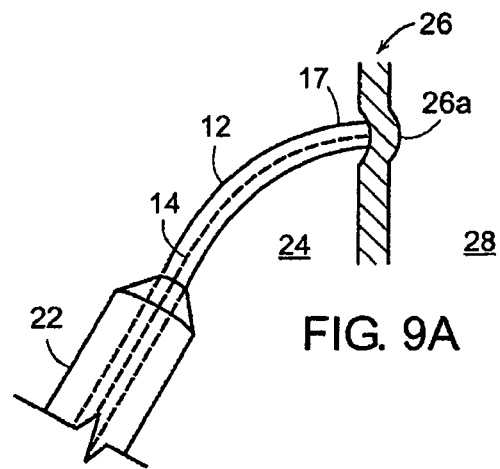
FIG. 9a-9g depicts the steps in an illustrative method for puncturing an atrial septum with an illustrative transseptal puncture device according to the invention.

In another aspect, the invention provides a method using a percutaneous approach for puncturing the atrial septum of a patient to treat, for example, patent foramen ovale or to gain access to the left atrium to ablate the left atrial appendage. FIGS. 9A-9E depict the steps of an illustrative method for puncturing an atrial septum with the transseptal puncture device according to the invention. The illustrative method includes the step of introducing an intravascular sheath 22 in a vessel to access the lumen of the right atrium 24. In an embodiment, the sheath 22 is tapered to enhance advancement of the sheath 22 though the atrial septum 26. Referring to FIG. 9A, after the sheath 22 is properly positioned in the right atrium 24, the outer needle 12 of the transseptal device 10 is advanced distally toward the atrial septum 26 and positioned against septum primum 26a at the puncture site. The blunt distal end 17 of the outer needle 12 is then pushed against septum primum 26a until some tenting of the atrial septum 26 is visible. The tenting should be sufficient to correctly identify the puncture site in the septum primum 26a. Alternatively, visualization techniques such as, three-dimensional echocardiogram or magnetic resonance imaging can be used that may work without tenting. Some amount of tenting also assists with the puncture itself.

Figure 9B:
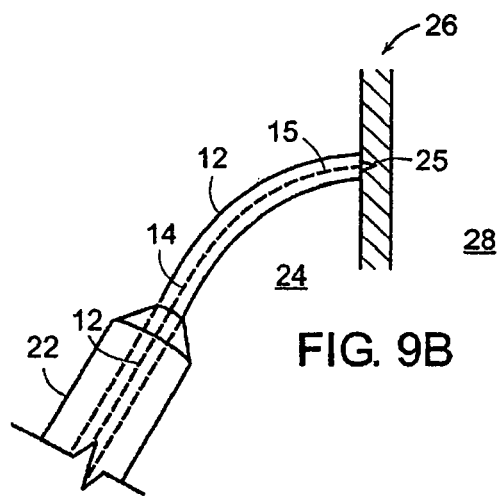

Referring to FIG. 9B, once the outer needle 12 is positioned, the inner needle 14 is advanced relative to the outer needle 12 through the septum 26. At its most distal position, about 10 mm of the inner needle 14 should extend from the distal end 17 of the outer needle 12. Alternatively, the most distal position could be about 30 mm, if the distal portion 15 of the inner needle 14 had a hook shape, as is shown in FIG. 8. In an embodiment, the transition from the hook portion to the straight portion of the inner needle 14 is exposed. The outer needle 12 follows the path of the inner needle 14 through the septum 26. Because of the fine diameter, extreme sharpness, and the added stiffness provided by the outer needle 12, the inner needle 14 can be initially advanced into the septum 26. The motion of the inner needle 14 may be forward, vibrating, reciprocating, linear, or rotational, for example. In one embodiment, movement of the inner needle 14 is accomplished manually. Alternatively, movement of the inner needle 14 may be automated and therefore require additional controls such as a spring-loaded needle to be attached to the delivery system components such as the sheath 22. Such devices of the invention are easier for the doctor to manipulate and safer for the patient.

Figure 9C:
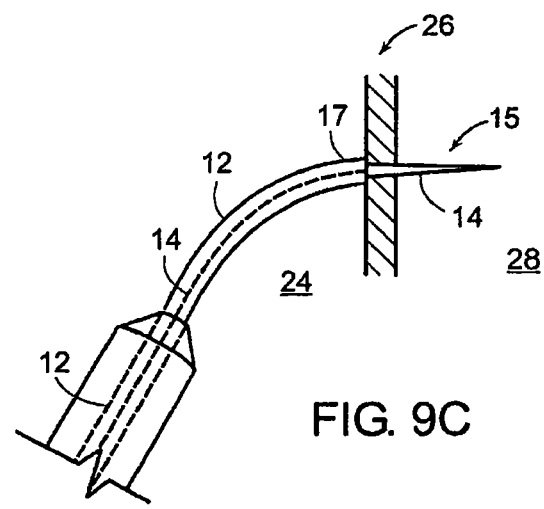
Figure 9D:
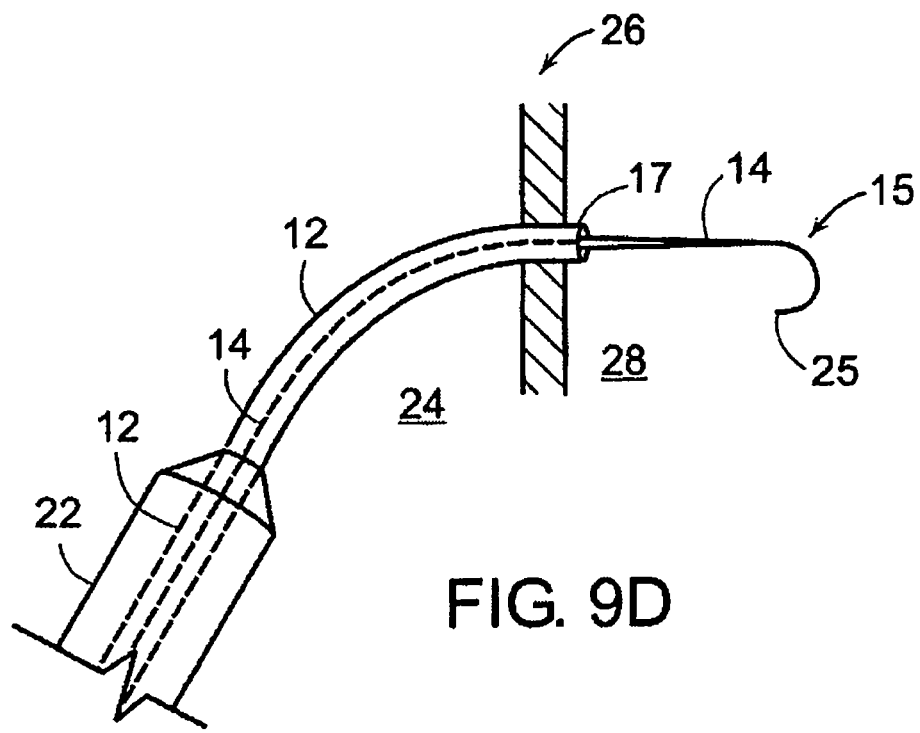
Figure 9E:
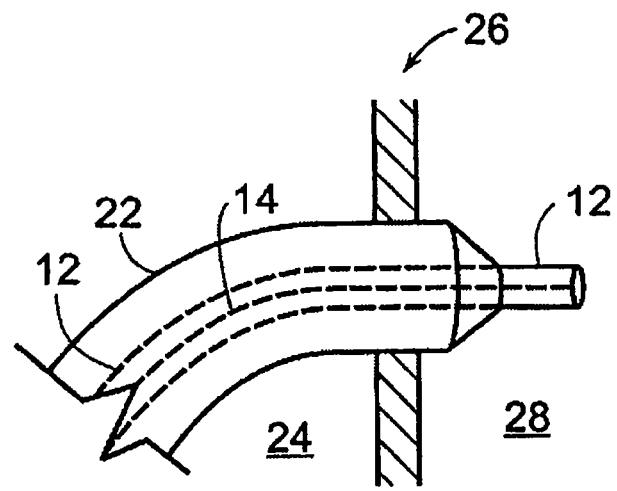
Figure 9F:
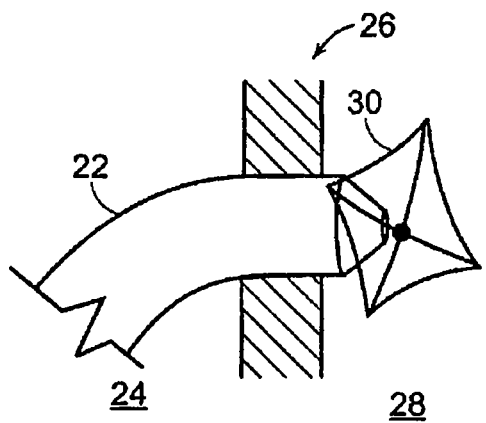
Figure 9G:
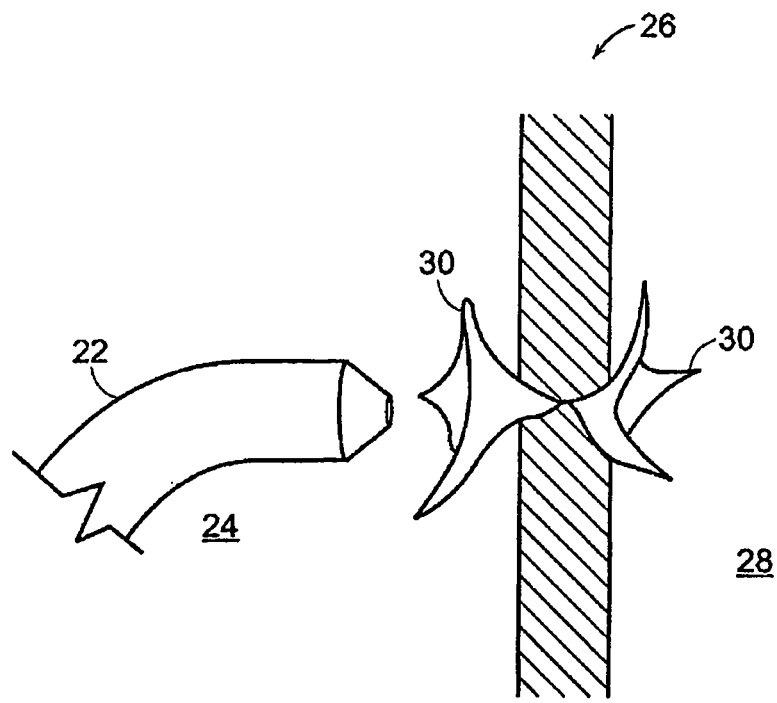

Referring now to FIG. 9C, once the distal end 15 of the inner needle 14 is positioned within the septum 26, the tissue provides support to the exposed part of the inner needle 14 until the whole tip of the inner needle 14 is delivered into the left atrium 28. Referring to FIG. 9D, the outer needle 12 is advanced and positioned in the left atrium 28. Referring to FIG. 9E, standard catheterization laboratory procedures are utilized to place the sheath 22 within the left atrium 28. Once the sheath 22 is in the left atrium 28, the other components of the device, for example, the inner needle 14 and the outer needle 12, can be completely removed from the sheath 22 and the sheath 22 can be used to deliver implants, for example, such as an atrial occluder for the treatment of a patent foramen ovale, sutures, or other intracardiac therapeutic devices. For example, referring to FIG. 9F, one half of an occluder 30 is released from the sheath 22 and positioned in the left atrium 28. Referring to FIG. 9G, the sheath 22 is then withdrawn into the right atrium 24 and the other half of the occluder 30 is released and positioned in the right atrium 24. In an embodiment, the inner needle 14 is left behind, traversing the puncture site, and acts to maintain the puncture site as well as to act as a guidewire (e.g., and the other outer needle 12 is withdrawn). In another embodiment, the inner needle 14 is withdrawn, e.g., into the outer needle 12.

The method for transseptal puncture using the transseptal device described herein is advantageous over conventional methods. For example, when using the devices and methods of the invention inadvertent contact of the inner needle 14 with the left atrial free wall (not shown) immediately after the septum 26 is punctured does not result in damage to or perforation of the left atrial free wall because the distal end 15 of the inner needle 14 is very flexible, as illustrated, for example, in FIG. 4 and corresponding text, or has an alternative tip 25, as illustrated, for example, in FIG. 8 and corresponding text, when fully extended from the distal opening 18 of the outer needle 12. When the distal end 15 of the inner needle 14 contacts the left atrial free wall, the distal end 15 of the inner needle 14 harmlessly bends rather than perforates the left atrial free wall. In one embodiment, the distal end 15 of the inner needle 14 bends because of the enhanced flexibility of the inner needle 14 at the intermediate portion 16, as described above in connection with FIGS. 4-8, between the proximal portion 11 and distal portion 15 of the inner needle 14. In an embodiment, perforation of the left atrial wall is avoided by modifying the shape of the inner needle 14 to form, for example, a hook or a bend.

Another advantage of the transseptal puncture devices described herein is the ability of the device to puncture through thick septum such as septum secundum. The transseptal puncture devices according to the invention can be used for remote suturing of a PFO or other defects that may be accessed percutaneously.

The transseptal puncture device according to the invention can also be used with various atrial septal defect locators such as those described in U.S. Ser. No. 10/660,444. For example, the locator may stabilize (e.g., constrain) the motion of the septa during insertion of the inner needle. Generally, a locator system includes a plurality of flexible members, at least one flexible member positionable on a side of the tissue opposite to another flexible member.

Figure 10:
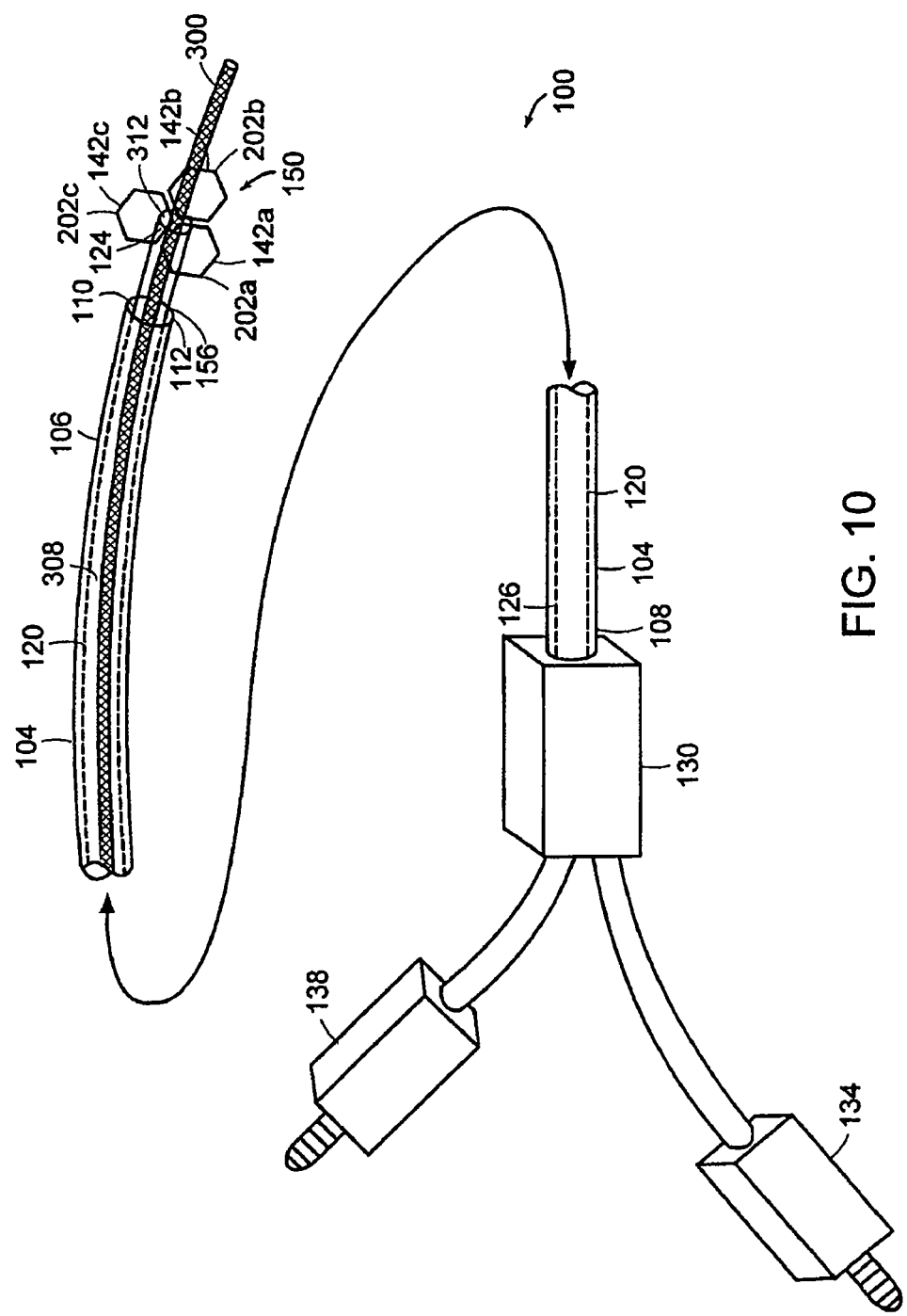
FIG. 10 is a fragmented illustration of a septal puncture apparatus according to an illustrative embodiment of the invention.

FIG. 10 illustrates a septal puncture apparatus 100 including three flexible members 142a, 142b, and 142c (generally 142) coupled to a delivery member 120 for applying, e.g., a pressure or force to a region in a body by pushing, pulling, or restraining the tissue, thereby stabilizing the tissue. The flexible members 142a, 142b, and 142c may be hexagonal in shape and coupled to a distal end 124 of the delivery member 120, thereby forming, generally, a planar array 150. The delivery member 120 is slideably receivable within a lumen 110 of the elongate member 104. Instruments, e.g., the delivery member 120 and a cutting member 300 (e.g., a member that perforate the tissue, which can comprise, referring to FIG. 1, an inner needle 14 and/or an outer needle 12, for example), are slideably receivable in the lumen 110 of the elongate member 104. In this embodiment, the cutting member 300 is slideably receivable in a lumen 308 of the delivery member 120 and extends distally or withdraws proximally from an opening 312 at the distal end 124 of the delivery member 120.

FIG. 10 also illustrates an exemplary interface 130 that permits controllers, for example, a set of apparatus controllers 134 and 138 to communicate with the elongate member 104 and the delivery member 120, respectively. The exemplary controllers 134 and 138 extend, retract, or otherwise manipulate, e.g., the elongate member 104 and the delivery member 120, respectively. A single controller, could, alternatively, control all functions and operations of the tissue puncture apparatus 100 and the instruments disposed therein.

By way of example, the elongate member 104 and the delivery member 120 are flexible tubes fabricated from a biocompatible material, e.g., polyethylene, polyether-amide block co-polymer (PEBAX™), polyurethane, or fluorinated ethylene propylene.

By way of example, the flexible members 142 are manufactured using nickel-titanium material, such as Nitinol™ (Nitinol Devices and Components, Freemont, Calif.), or other shape memory alloy materials. The nickel-titanium wire, when properly manufactured, exhibits elastic properties for the wire to be manipulated (e.g., bent) by an operator and then returned to, substantially, the same shape the wire possessed prior to it being manipulated.

Figure 11:
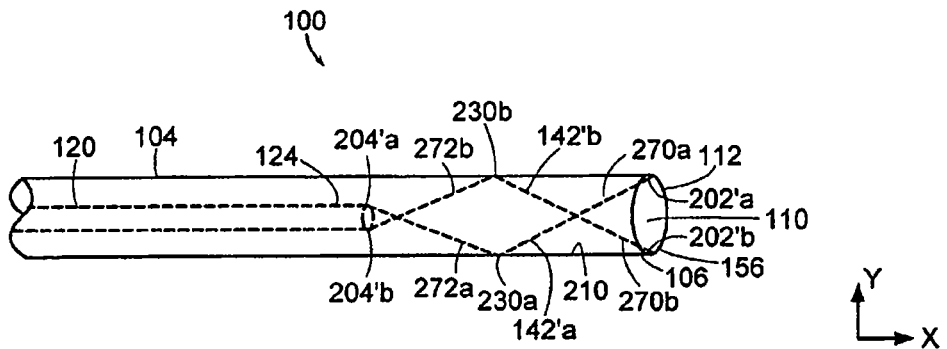
FIG. 11 is a schematic side view of a portion of a septal puncture apparatus including a set of flexible members according to an illustrative embodiment of the invention.

Alternatively, FIG. 11 illustrates a portion of a septal puncture apparatus 100 including exemplary flexible members 142'a and 142'b, which each include a leg such as a wire having a first end 204'a and 204'b, respectively, joined to the distal end 124 of the delivery member 120. Each of the flexible members 142'a and 142'b also have a second distal end 202'a and 202'b, respectively, that is free, i.e., not joined to any other structure of the septal puncture apparatus 100. The longitudinal axis of the flexible members 142'a and 142'b are oriented substantially parallel to the elongate member 104 when the flexible members 142'a and 142'b are located within the lumen 110 of the elongate member 104. The flexible members 142'a and 142'b have a first portion 272a and 272b, respectively and a second portion 270a and 270b, respectively. The flexible members 142'a and 142'b are disposed within the lumen 110 in a contracted position such that the second ends 202'a and 202'b are directed distally towards the opening 112 in the distal end 106 of the elongate member 104. The flexible members 142'a and 142'b are freed from the confines of the lumen 110 by moving the flexible members 142'a and 142'b between the contracted position illustrated, for example, in FIG. 11 and an extended position, such as the extended position depicted in FIG. 12B. After insertion into the lumen 110 of the elongate member 104, the flexible members 142'a and 142'b apply a force to an inner surface 210 of the elongate member 104 in a first location 230a and 230b, respectively, on the inner surface 210 of the lumen 110 that the flexible members 142'a and 142'b contact.

Figure 12A:
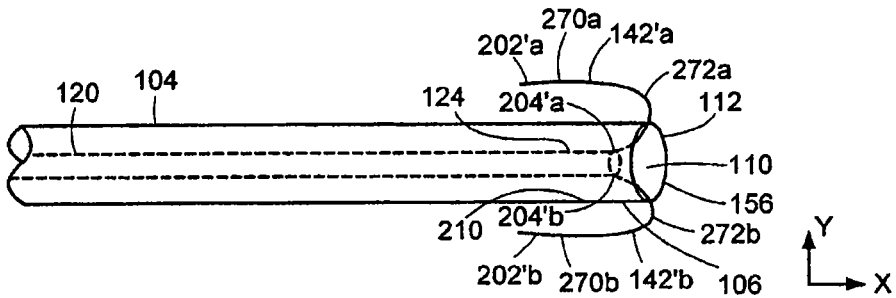
FIG. 12A is a schematic side view of a portion of an embodiment of a septal puncture apparatus including a set of flexible members partially extended from an elongate member.
Figure 12B:
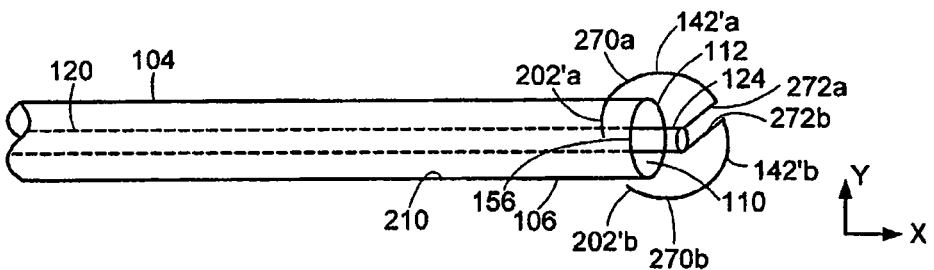
FIG. 12B is a schematic side view of the flexible members of FIG. 12A fully extended from the opening in the elongate member.

Referring now to FIG. 12A, as the delivery member 120 is extended out of the opening 112 of the elongate member 104, the second ends 202'a and 202'b of the flexible members 142'a and 142'b, respectively, undergo an articulation and point, generally, in a proximal direction toward the handle (not shown). Referring now to FIG. 12B, the elongated delivery member 120 is further extended distally along the lengthwise dimension (in the positive direction along the X-axis) of the lumen 110 until the distal end 124 of the delivery member 120 emerges from the opening 112 of the elongate member 104. The second ends 202'a and 202'b of the exemplary preshaped flexible members 142'a and 14'b, respectively, undergo an additional articulation and as a result point, generally, towards one another. In this extended position, each of the flexible members 142'a and 142'b is substantially planar in shape.

Alternatively, the second ends, for example, the second ends 202'a and 202'b, may have a different diameter than other locations along the length of the flexible elastic members 142'a and 142'b. By way of example, an operator may select an apparatus having flexible members that have second ends 202'a and 202'b having a larger diameter to, for example, reduce trauma to tissue the second ends 202'a and 202'b contact during use. Alternatively, the second ends 202'a and 202'b may have a ball shaped tip.

Figure 13:
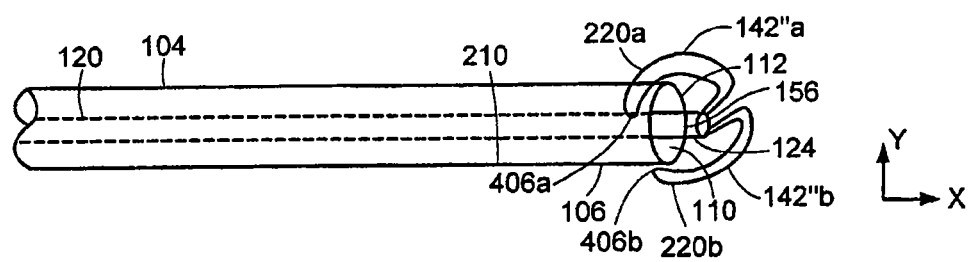
FIG. 13 is a schematic side view of another embodiment of a set of flexible members according to the invention.

FIG. 13 depicts exemplary flexible members 142"a and 142"b that include a first wire loop section 220a and a second loop section 220b, respectively. The tip 406a and 406b of the loop sections 220a and 220b, respectively, point, generally, towards one another and towards the delivery member 120. Loop sections 220a and 220b may, alternatively, be oriented in a variety of directions (e.g., away from the delivery member 120 or at a 45 degree angle away from the delivery member 120).

Referring now to FIGS. 14A and 14B, a septal puncture apparatus 100 includes a single flexible member 142''' that has a middle section 540 located, generally, intermediate the first end 206 and the second end 208 of the flexible member 142'''. The flexible member 142''' thereby forms a closed loop. In this embodiment, the flexible member 142''' is configured so the middle section 540 is located, generally in the center of a plane defined by the flexible member 142''' as illustrated by the end-on view of FIG. 14B. In this configuration, the middle section 540 of the flexible member 142''' aids with stiffening the flexible member 142''', which minimizes bending when, for example, the flexible member 142''' is used by an operator to apply forces to a tissue, e.g., the atrial septum. In this configuration, the flexible member 142 forms a closed loop that is sized and shaped, for example, to contact a first and second side of a tissue.

Referring now to FIGS. 15A and 15B, the flexible elastic member 142''' is a coil and has a spiral shape. By way of example, in use, a portion 1410 of the flexible member 142'''' can be located on a first side of a tissue and a portion 1420 of the flexible member 142'''' can be located on a second side of a tissue. For example, the flexible member 142'''' can be screwed through a tunnel or a hole, such as a defect in the atrial septum. Alternatively, the distal end 124 of the delivery member 120 may be located axially through, for example, a hole in a tissue such that the flexible member 142'''' may be withdrawn partially through the hole by a rotational (screwlike) motion of the delivery member 120 thereby locating the portion 1410 of the flexible member 142'''' on a first side of the tissue and the portion 1420 of the flexible member 142'''' on a second side of a tissue.

Referring to FIG. 16A, the delivery member 120 is translated axially along the lengthwise dimension of the lumen 110 until the distal end 124 of the delivery member 120 emerges from an opening 112 in the elongate member 104 and the flexible members 142a, 142b, and 142c transition from the contracted first position 330 shown in FIG. 16A to a second extended position 340 shown in FIG. 16B. The exemplary flexible members 142a, 142b, and 142c expand to assume, for example, substantially hexagonal shapes upon emerging from the opening 112 in the elongate member 104 and expanding. The extended flexible members 142a, 142b, and 142c are substantially planar. The plane defines a plurality of axes that lie in the plane and the plurality of axes are non-parallel to (i.e., biased relative to) the elongate member 104. An angle 344 defined by at least one of the plurality of axes of the plane of the flexible members 142a, 142b, and 142c and the longitudinal axis of the elongate member 104 is typically specified (e.g., by an operator) such that the flexible members 142a, 142b, and 142c are flush with tissue surface and are capable of applying a force across a large tissue area. For example, the angle 344 might be chosen to ensure the flexible members 142a, 142b, and 142c conform to the shape of a tissue surface abutting the flexible members 142a, 142b, and 142c. If the force is applied, e.g., across a large tissue area the movement of the tissue in any location across the tissue area will be minimized. The flexible members 142a, 142b, and 142c could, alternatively, be of any shape (e.g., polygonal, circular, or ellipsoidal) or of any quantity (e.g., one, two, or five) where the shape and/or quantity of the flexible members 142a, 142b, and 142c are typically selected to distribute as much force as possible while still being able to fit within the lumen 110 of the elongate member 104 and emerge from or retract into the lumen 110.

When the flexible members 142a, 142b, 142c are extended in the second expanded position 340 upon emerging from the opening 112, the exemplary cutting member 300 extends axially in the lumen 308 of the delivery member 120 until a cutting tip 304 of the cutting member 300 emerges from the opening 312 in the distal end 124 of the delivery member 120. The tip 304 of the cutting member 300 cuts the tissue in close proximity to the opening 312 of the delivery member 120.

Figure 17:
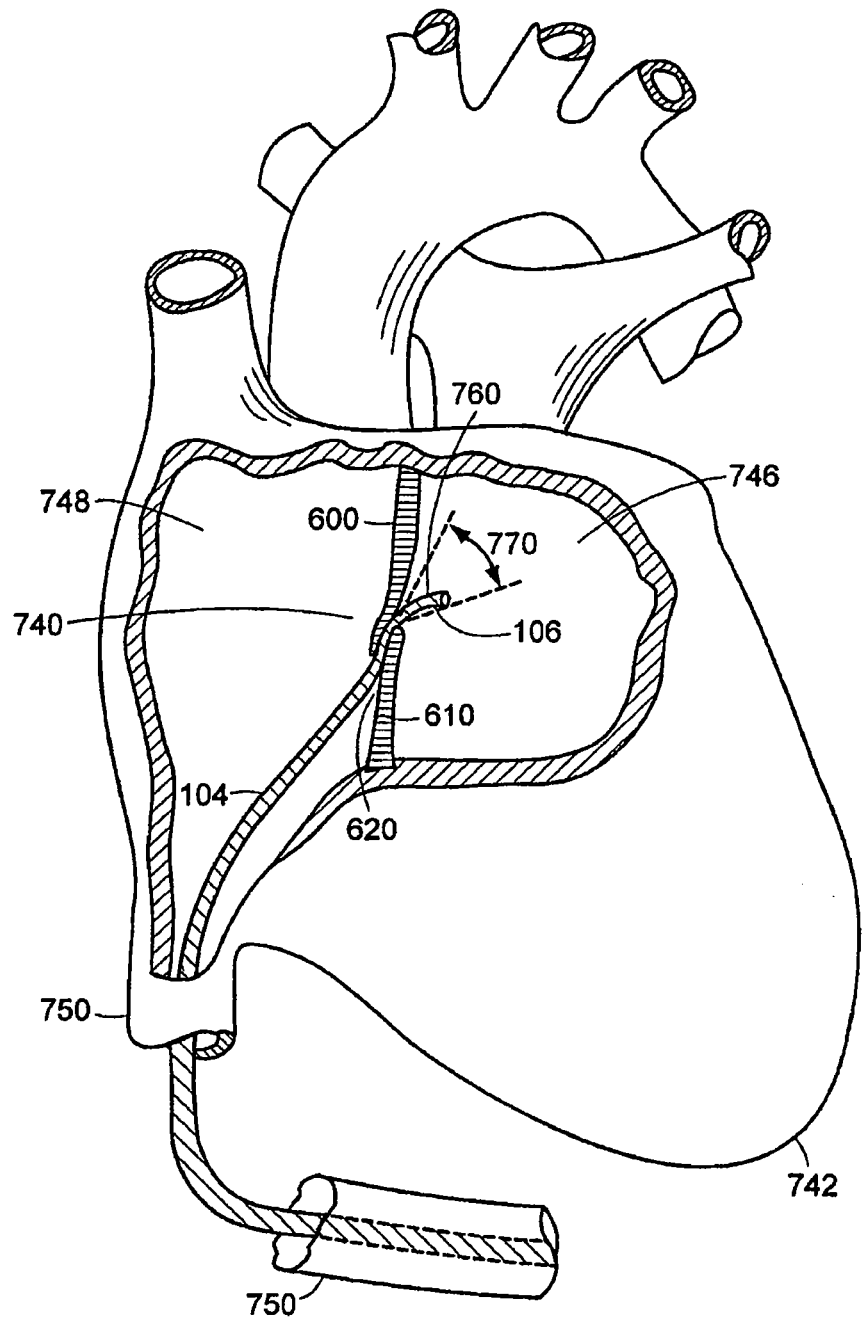
FIG. 17 is a partially broken-away view of a heart depicting a portion of a septal puncture apparatus, according to the invention, on a second side of the septal wall.

Referring now to FIG. 17, an operator introduces an elongate member 104 into the right atrium 748 of a heart 742 through the descending vena cava 750. The elongate member 104 is advanced distally until the distal end 106 of the elongate member 104 passes through a defect 620 (for example, a patent foramen ovale) in the septum 740. The distal end 106 of the elongate member 104 is shown at an angle 770 of about 45 degrees relative to the longitudinal axis of the elongate member 104 due to a bend 760 in the distal end of 106 of the elongate member 104. The bend 760 in the elongate member 104 may be mechanically pre-formed or pre-bent at the angle 770 between about 0 degrees and about 180 degrees prior to insertion of the elongate member into the body. The bend 760 could, alternatively, be accomplished by heating a nickel-titanium material or other shape memory alloy located within the distal end 106 of the elongate member 104.

Figure 18A:
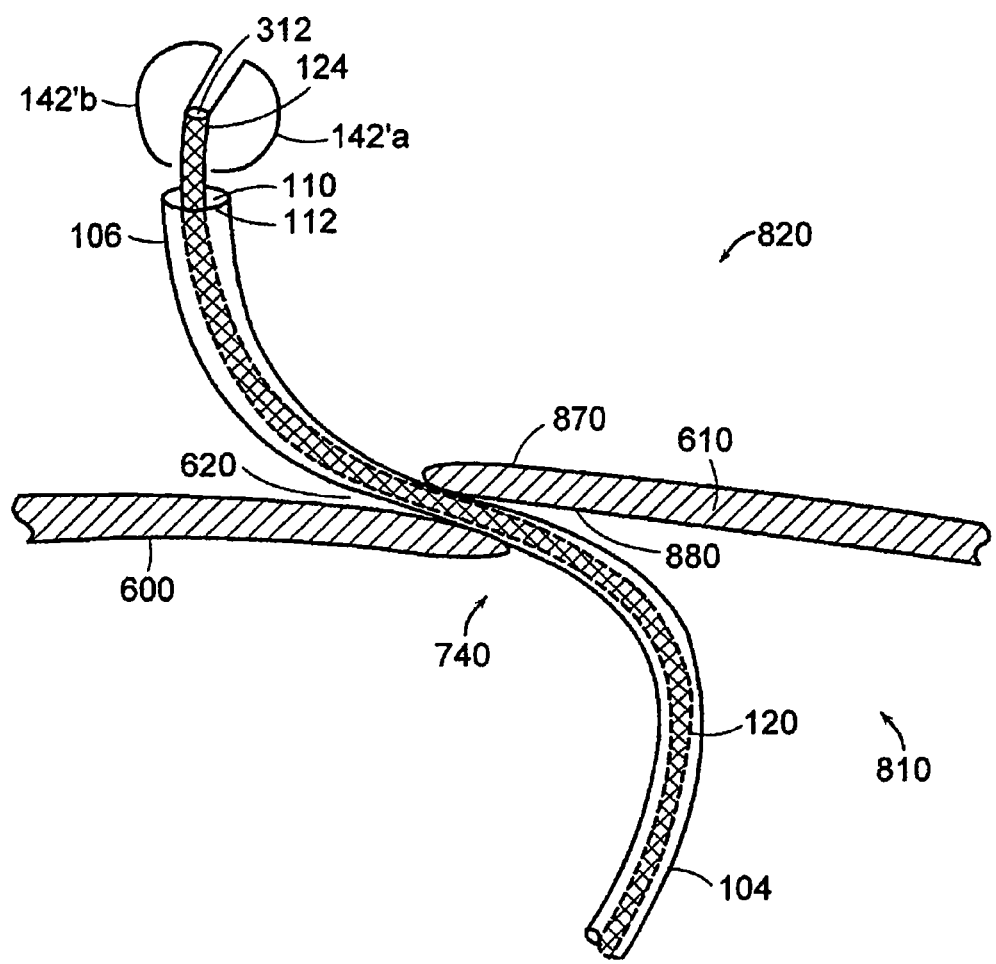
FIG. 18A is a cross-sectional view of a septal wall of a heart depicting a set of flexible members located outside an opening in an end of an elongate member, according to an illustrative embodiment of the invention.
Figure 18B:
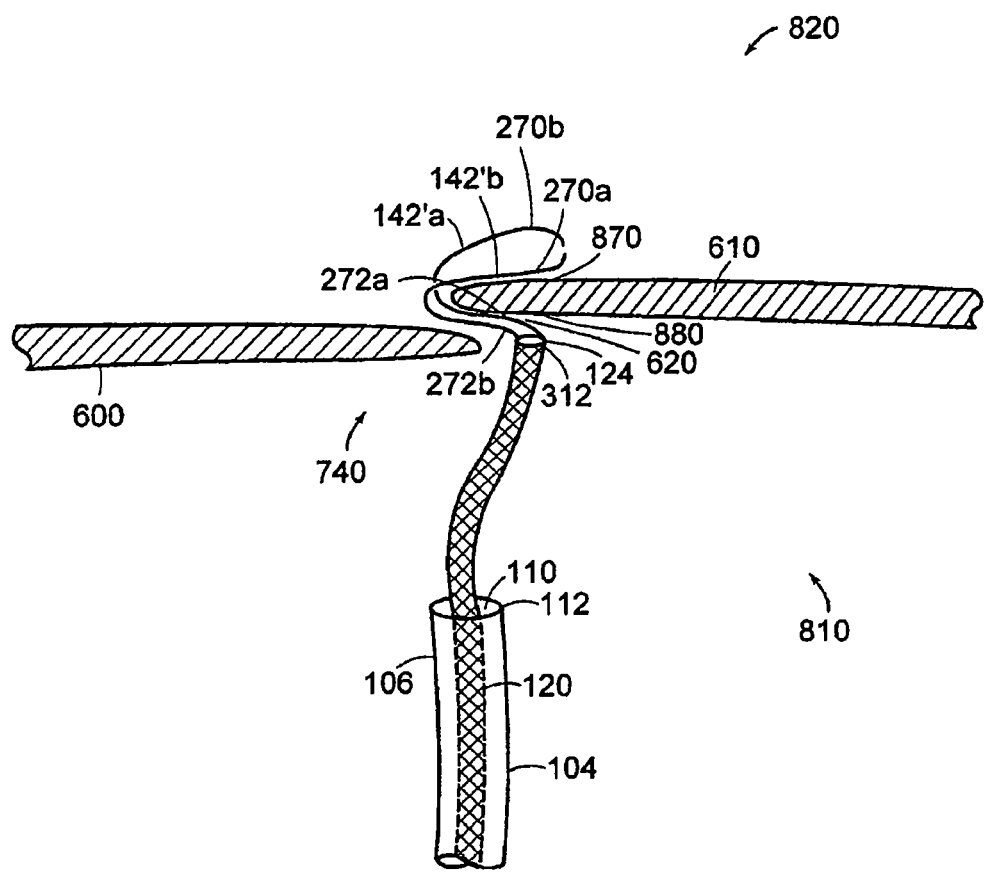
FIG. 18B is a cross-sectional view of the flexible members of FIG. 19A in which a portion of the flexible members is located in contact with a first side of a septal wall and another portion of the flexible members is located in proximity to a second side of the septal wall.
Figure 18C:
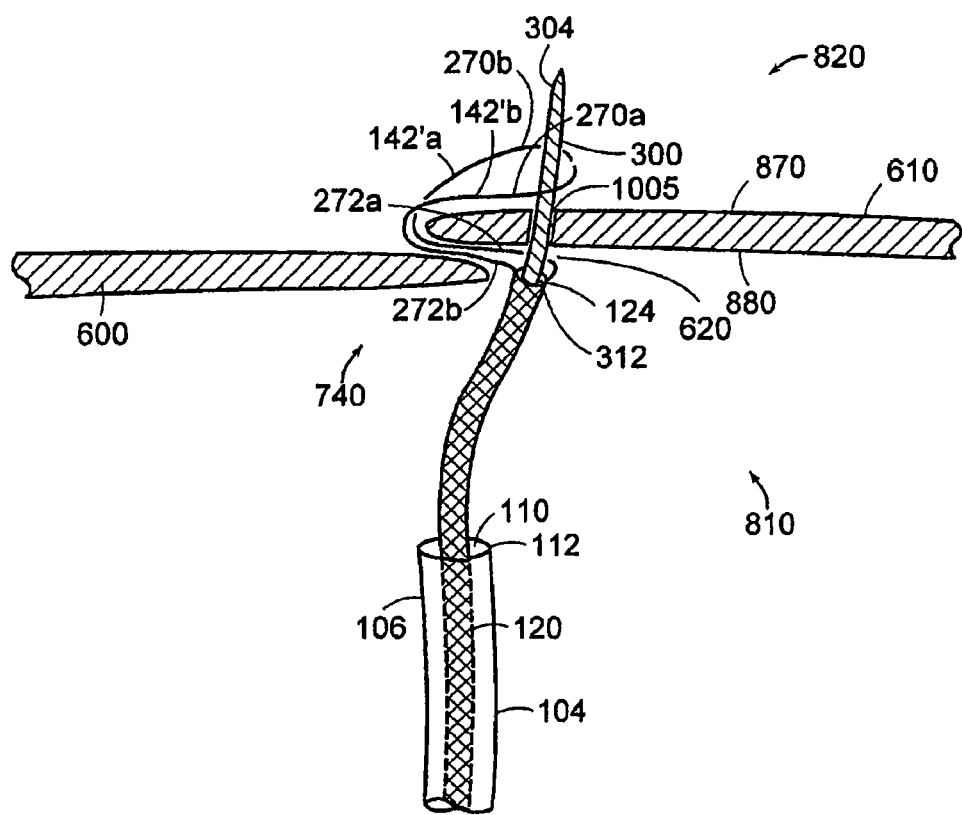
FIG. 18C is a cross-sectional view of the flexible members of FIGS. 19A and 19B in which a cutting member is extended from a lumen in the delivery member creating a hole through the septal wall.

The septal puncture apparatus shown in FIGS. 18A, 18B, and 18C includes two flexible members 142'a and 142'b coupled to the distal end 124 of the delivery member 120. The flexible members 142'a and 142'b are initially located within the lumen 110 of the elongate member 104. An operator initially guides the distal end of 106 of the elongate member 104 through the defect (hole) 620 such that the distal end 106 is located on a second side 820 (in the left atria of the heart) of the septum secundum 600 and septum primum 610. Now referring to FIG. 18A, the operator then extends the flexible members 142'a and 142'b as described herein with respect to, for example, FIGS. 12A and 12B.

With continued reference to FIG. 18A, the elongate member 104 is retracted proximally until the distal end 106 of the elongate member 104 passes back through the defect 620 and is positioned on the first side 810 of the septum 740.

The delivery member 120 is then retracted proximally so the second portions 270a and 270b of the flexible members 142'a and 142'b and the distal end 124 of the delivery member 120 are in close proximity to the defect 620, the septum primum 610, and the septum secundum 600 on the second side 820 of the septum 740.

Now referring to FIG. 18B, as the delivery member 120 is further retracted proximally such that the distal end 124 of the delivery member 120 is withdrawn through the defect 620 until it is in contact with or in close proximity to the first surface 880 of the septum primum 610 on the first side 810 of the septum primum 610. The second portions 270a and 270b of the flexible members 142'a and 142'b are positioned, generally non-parallel to the longitudinal axis of the elongate member 104 and are in physical contact with at least the second surface 870 of the septum primum 610 on the second side 820 of the septum primum 610 and also partially located within the defect 620 in the septum 740. The first portions 272a and 272b of the flexible members 142'a and 142'b are located on the first side 810 of the septum 740. Accordingly, the flexible members 142'a and 142'b are sized and shaped for contact with the first side 810 and the second side 820 of the septum 740. The flexible members 142'a and 142'b are thus capable of limiting movement of the septum primum 610. Now referring to FIG. 18C, the cutting member 300 is extended from the opening 312 in the distal end 124 of the delivery member 120. The cutting tip 304 of the cutting member 300 introduces a hole 1005 (tissue opening) through the septum primum 610.

Figure 19:
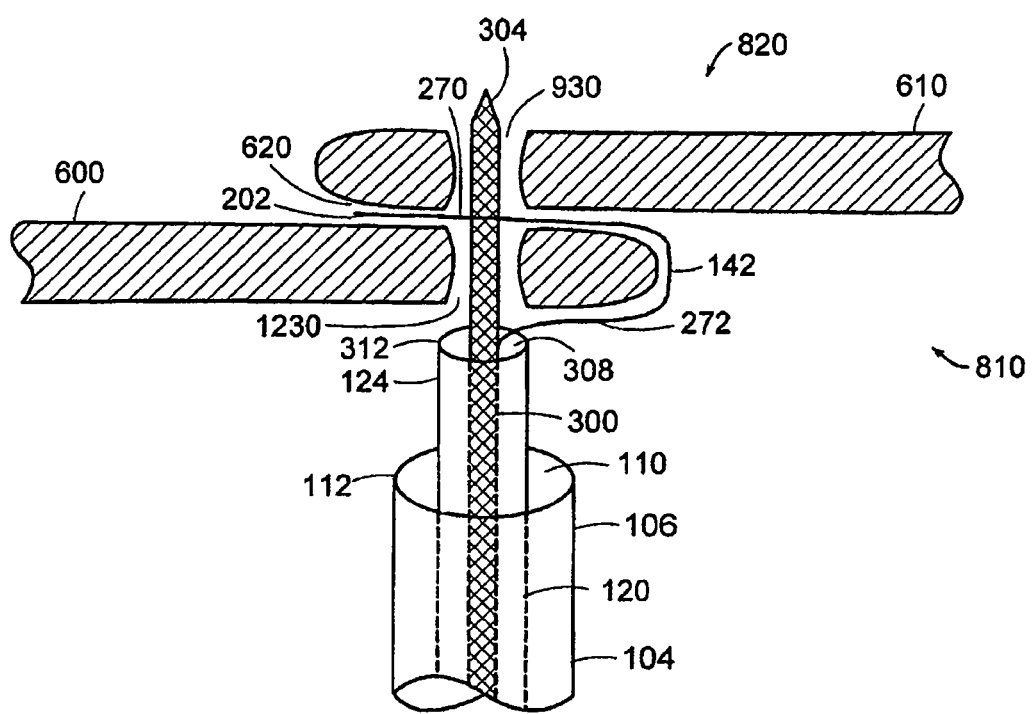
FIG. 19 is a schematic side view of a flexible member, a cutting member, and an elongate member according to an illustrative embodiment of the invention.

Referring now to FIG. 19, an exemplary flexible member 142 is attached to the distal end 124 of the delivery member 120, which extends from the opening 112 in the distal end 106 of the elongate member 104. The delivery member 120 and the elongate member 142 are located on the first side 810 of the septum secundum 600. The distal end 124 of the delivery member 120 is located in close proximity to the tissue surface of the septum secundum 600 on the first side 810 of the septum secundum 600. The flexible member 142 extends through the hole 620 between the septum primum 610 and the septum secundum 600 from the first side 810 to the second side 820. The first side 810 of the septum primum 610 opposes the second side 820 of the septum primum 610. The flexible member 142 is positioned so that the second end 202 and second portion 270 of the flexible member 142 are located on the second side 820 of the septum secundum 600 and the first portion 272 of the flexible member 142 is located on the first side 810 of the septum secundum 600. In this configuration, the flexible member 142 is thus capable of limiting movement of the septum secundum 600. In this embodiment only the septum secundum 600 is secured to limit movement. In alternative embodiments, however, the septum secundum 600 and/or the septum primum 610 may be secured to limit movement.

Additionally, it should be noted that Applicants intend any operable embodiments existing between the devices, methods and applications thereof disclosed in the illustrative embodiments described above to be considered within the scope of the inventions disclosed herein and, as such, claimable subject matter.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

INCORPORATION BY REFERENCE

All publications and patent documents cited in this application are incorporated by reference in their entirety for all purposes to the same extent as if the contents of each individual publication or patent document was incorporated herein.

What is claimed is:

1. A transseptal puncture device for puncturing the atrial septum of a patient, comprising:
    a solid inner needle configured for placement within a lumen of a needle configured to transverse the septum and moveable beyond the distal end of the needle, the solid inner needle including a proximal portion, an intermediate portion, and a distal portion;
    wherein the solid inner needle is formed substantially of Nitinol;
    wherein the intermediate portion is more flexible than the proximal portion and has a circumference equal to that of the proximal portion;
    wherein the distal portion is generally curved, is more flexible than the proximal portion, and includes a tip configured to pierce the atrial septum; and
    wherein the distal portion has sufficient stiffness such that it is configured to penetrate the atrial septum when the distal portion substantially resides within the needle and has insufficient stiffness such that it is configured to not penetrate cardiac tissue when the distal portion resides substantially outside of the needle.

2. The transseptal puncture device of claim 1, wherein the intermediate portion has been annealed at 500° C.

3. The transseptal puncture device of claim 1, wherein the intermediate portion of the solid inner needle is formed using a first process that includes a heat-treatment at a first temperature and the other portions of the solid inner needle is formed using a second process that includes a heat-treatment at a second temperature, wherein the first and second temperatures are different and the intermediate portion and the other portions of the solid inner needle formed by the second processes have different flexibility properties.

4. The transseptal puncture device of claim 1, wherein a distal tip portion of the distal portion is generally straight.

5. The transseptal puncture device of claim 1, wherein a distal tip portion of the distal portion is bent.

6. The transseptal puncture device of claim 1, wherein at least part of the distal portion forms a hook shape.

7. The transseptal puncture device of claim 1, wherein the distal portion is curved about 180°.

8. The transseptal puncture device of claim 1, wherein the intermediate portion has an outer diameter ranging from about 0.1 mm to about 0.5 mm.

9. The transseptal puncture device of claim 1, wherein the distal portion includes a cut-away portion.

10. The transseptal puncture device of claim 1, wherein at least one of the distal portion and the intermediate portion has a cross-sectional area that is smaller than the cross-sectional area of the proximal portion.

11. The transseptal puncture device of claim 1, wherein the distal portion has a longitudinal length ranging from about 5 mm to about 30 mm.

12. The transseptal puncture device of claim 1, wherein the distal portion has a longitudinal length ranging from about 10 mm to about 20 mm.

13. The transseptal puncture device of claim 1, wherein the intermediate portion is generally straight.

14. The transseptal puncture device of claim 1, wherein the intermediate portion has a longitudinal length ranging from about 0.5 mm to about 30 mm.

15. The transseptal puncture device of claim 1, wherein the intermediate portion has a longitudinal length ranging from about 10 mm to about 20 mm.

16. The transseptal puncture device of claim 1, wherein the nominal cross-sectional area of the solid inner needle at any first location along the length of the intermediate portion or the distal portion is equal to or greater than the nominal cross-sectional area of the solid inner needle at any second location distal of the first location.

17. The transseptal puncture device of claim 16, wherein the nominal cross-sectional area of the solid inner needle at any first location along the length of the proximal portion, the intermediate portion, or the distal portion is equal to or greater than the nominal cross-sectional area of the solid inner needle at any second location distal of the first location.

18. The transseptal puncture device of claim 1, wherein the intermediate portion of the solid inner needle includes slits.

19. A transseptal puncture device for puncturing the atrial septum of a patient, comprising:
    a solid inner needle configured for placement within a lumen of a needle configured to transverse the septum and moveable beyond the distal end of the needle, the solid inner needle including a proximal portion, an intermediate portion, and a distal portion;
    wherein the solid inner needle is formed substantially of Nitinol;
    wherein the intermediate portion is more flexible than the proximal portion and has a circumference equal to that of the proximal portion;
    wherein the distal portion is generally curved, is generally thinner than the intermediate portion, and includes a tip configured to pierce the atrial septum;
    wherein the distal portion has sufficient stiffness such that it is configured to penetrate the atrial septum when the distal portion substantially resides within the needle and has insufficient stiffness such that it is configured to not penetrate cardiac tissue when the distal portion resides substantially outside of the needle; and
    wherein at least part of the distal portion is substantially ellipsoidal.

20. The transseptal puncture device of claim 19, wherein the ellipsoidal distal region has a thinner outer dimension and a thicker outer dimension, and at least part of the intermediate portion has an outer diameter that is less than the thicker outer dimension and is greater than the thinner outer dimension.

21. The transseptal puncture device of claim 19, wherein the intermediate portion of the solid inner needle includes slits.

22. A transseptal puncture device for puncturing the atrial septum of a patient, comprising:
    a solid inner needle configured for placement within a lumen of a needle configured to transverse the septum and moveable beyond the distal end of the needle;
    wherein the solid inner needle includes a proximal portion, an intermediate portion, and a distal portion having a tip configured to pierce the atrial septum;
    wherein the solid inner needle is formed substantially of Nitinol;

wherein the intermediate portion is more flexible than the proximal portion and has a circumference equal to that of the proximal portion;

wherein the distal portion has sufficient stiffness such that it is configured to penetrate the atrial septum when the distal portion substantially resides within the needle and has insufficient stiffness such that it is configured to not penetrate cardiac tissue when the distal portion resides substantially outside of the needle; and wherein the distal portion has a central axis biased in a curved configuration to define a distal curve such that the solid inner needle forms a curved configuration when at least part of the distal portion extends beyond the distal end of the needle and assumes a generally straight configuration when the distal portion resides within the lumen of the needle.

23. The transseptal puncture device of claim 22, wherein the distal portion of the solid inner needle comprises a distal tip portion that deviates from the linear path of the solid inner needle when not constrained within the lumen of the needle.

24. The transseptal puncture device of claim 22, wherein the distal portion, when residing generally outside the lumen of the needle, forms at least one of a curve shape and a hook shape.

25. The transseptal puncture device of claim 22, wherein the device is moveable between a piercing configuration in which at least part of the distal portion of the solid inner needle is located within the lumen of the needle and a non-piercing configuration wherein at least part of the intermediate portion is located outside the lumen of the needle.

26. The transseptal puncture device of claim 22, wherein the intermediate portion of the solid inner needle includes slits.

* * * * *